US006353024B1

(12) United States Patent
Grouhel et al.

(10) Patent No.: US 6,353,024 B1
(45) Date of Patent: Mar. 5, 2002

(54) METHOD FOR PREVENTING AND TREATING ARTHRITIS, OSTEO-TRAUMATIC PAIN, AND NEURALGIAS WITH TRIMEBUTINE

(75) Inventors: Agnès Grouhel, Meudon; Gilles Brunelle, Antony; François Roman, Vitry-sur-Seine; Jacques Hamon, Orsay, all of (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/490,093

(22) Filed: Jan. 24, 2000

(51) Int. Cl.⁷ .............................................. A61K 31/24
(52) U.S. Cl. ...................................... 514/534
(58) Field of Search ........................ 514/534

(56) References Cited

FOREIGN PATENT DOCUMENTS

| FR | 2.369 M | 10/1962 |
| WO | 99/01417 | 2/1999 |

OTHER PUBLICATIONS

Ma et al, Chemical Abstracts, vol. 132, abstract No. 117407, 1999.*
Lecheze et al, Chemical Abstracts, vol. 129, abstract No. 285931, 1998.*
Schaffstein et al, Biological Abstracts, vol. 89, abstract No. 74779, 1990.*
Allescher, et al. Interaction of Trimebutine and JO–1196 (fedotozine) with Opioid Receptors in the Canine Ileum, *J. Parmacol. Exp. Ther.*, vol. 257, No. 2, 1991, pp, 836–842.
Attal, et al., "Further Evidence for 'Pain–Related' behaviors in a Model of Unilateral Peripheral Mononeuropathy", *Pain*, vol. 41, 1990, pp. 235–251.
Bennett, et al., "A Peripheral Mononeuropathy in Rat that Produces Disorders of Pain Sensation Like Those Seen In Man", *Pain*, vol. 33, 1988, pp 87–107.
Berge, et al., "Pharmaceutical Salts", *J. Pharm. Sci.*, vol. 66, No. 1, Jan. 1977, pp 1–19.
Bueno, et al., "Effects of Orally vs. Parenterally administrated Trimebutine on Gastrointestinal and Colonic Motility in Dogs", *Gastroenterol Clin. Biol.*, vol. 11, 1987, pp. 90B–93B.
Calcutt, et al., "Tactile Allodynia and Formalin Hyperalgesia in Streptozotocin–Diabetic Rats: Effects of Insulin, Aldose Reductase Inhibition and Lidocaine", *Pain*, vol. 68, 1996, pp 293–299.
Cheng, et al., "Relationship Between the Inhibition Constant (Kr) and the Concentration of Inhibitor Which Causes 50 Per Cent Inhibition (150) of an Enzymatic Reaction", *Biochem. Parmacol.*, vol. 22, 1973, pp 3099–3108.
Courteix, et al., "Streptozocin–Induced Diabetic Rats: Behavioural Evidence for a Model of Chronic Pain", *Pain*, vol. 53, 1933, pp 81–83.
Delis, et al., "The Effect of Stress and an Opioid Agonist on Postprandial Motor Activity in the Human Small Bowel", *Gastroenterology*, vol. 106, 1994, p A485 (Abstract Only).
Dickenson, A.H., "Spinal Cord Pharmacology of Pain", *British J. Anesthesia*, vol. 75, 1995, pp 193–200.
Ghidini, et al., "Single Drug Treatment for Irritable Colon: Rociverine Versus Trimebutine Maleate", *Curr. Ther. Res.*, vol. 39, No. 4, Apr. 1985, pp 541–548.
Grandjouan, et al., "A Comparison of Metoclopramide and Trimebutine on Small Bowel Motility in Humans", *Aliment. Pharmacol. Ther.*, vol. 3, 1989, pp 387–393.
Julia, V. et al., "Influence de la trimebutine (Debridat) sur l'hypomotricite colique et les crampes abdominales liees a la distension rectale chez le rat", *Med. Chir. Dig.*, vol. 25, 1996, pp 239–242.
Lees, et al., "Studies on the Mechanism of Action of the Novel Anticonvulsant Lamotrigine (Lamictal) Using Primary Neuroglial Cultures from Rat Cortex", *Brain Res.*, vol. 612, pp 190–199.
Luttecke, K., "A three–part Controlled Study of Trimebutine in the Treatment of Irritable Colon Syndrome", *Cur. Med. Res. Op.*, vol. 6, No. 6, 1980, pp 437–443.
Matteson et al., "Na and Ca Channels in a Transformed Line of Anterior Pituitary Cells", *J. Gen. Physiol.*, vol. 83, 1984, pp 371–394
McPherson, G. A., "Analysis of Radioligand Binding Experiments", *J. Pharmacol. Methods*, vol. 14, 1985, pp 213–228.
Moshal, et al., "A Clinical Trial of Trimebutine (Mebutin) in Spastic Colon", *J. Int. Med. Res.*, vol. 7, 1979, pp 231–234.
Nagasaki, et al., "Effect of Trimebutine on Voltage–activated Calcium Currents in Rabbit Ileal Smooth Muscle Cells", *Br. J. Pharmacol*, vol. 110, 1993, pp 399–403.
Nagasaki, et al., "Effect of Trimebutine on K+ Current in Rabbit Ileal Smooth Muscle Cells", *European J. Pharmacol.*, vol. 235, 1993, pp 197–203.
*Pain*, Suppl. 3, 1986, S1–226.
Pascaud, et al., "Action de la trimebutine sur la motricite gastro–intestinale", *Gastroenterol Clin. Biol.*, vol. 11, 1987, pp 77B–81B.
Randall, et al., "A Method for Measurement of Analgesic Activity on Inflamed Tissue", *Arch. Parmacodyn.*, vol. 4, 1957, pp 409–419.
Roman, et al., "Interactions of Trimebutine with Guinea–pig Opioid Receptors", *J. Pharm. Pharmacol.*, vol. 39, 1987, pp 404–407.
Strichartz, et al., "The Action of Local Anesthetics on Ion Channels of Excitable Tissues", Local Anesthesics Handbook of Experimental Pharmacology, Springer–Verlag, Heidelberg, pp 21–52, 1987.

(List continued on next page.)

Primary Examiner—William R. A. Jarvis
(74) Attorney, Agent, or Firm—Charles W. Ashbrook

(57) ABSTRACT

The invention relates to the use of trimebutine [2-dimethylamino-2-phenylbutyl-3,4,5-trimethoxy-benzoate hydrogen maleate] or its corresponding stereoisomers for the preparation of a medicament to prevent and/or treat arthritis, osteo-traumatic pain, and neuralgias.

4 Claims, 16 Drawing Sheets

OTHER PUBLICATIONS

Tallarida, et al., "Manual of Pharmacological Calculations with Computer Programs", New York, Springer–Verlag, 1987.

Tomlinson, et al., "Functional Consequences of Streptozotocin–induced Diabetes Mellitus, with Particular Reference to the Cardiovascular System", *Pharmacol. Rev.*, vol. 44, 1992, pp 103–150.

Toussaint, et al., "Etude en simple aveugle de trimbutine et de la mebeverine dans le colon irritable et la dyspepsie", *Acta Ther.*, vol. 7, 1981, pp 261–268.

Turner, et al., "Prolonged Time Course of Glutamate Release from Nerve Terminals: Relationship Between Stimulus Duration and the Secretory Event", *J. Neurochem.*, vol. 64, 1995, pp 2022–2033.

Valmier, et al., "Expression of Voltage–dependent Sodium and Transient Potassium Currents in an Indentified Sub–population of Dorsal Root Ganglion Cells Acutely Isolated From 12–day–old Mouse Embryos", *Eur. J. Physiol.*, vol. 414, 1989, pp 360–368.

Wang. et al., "Localization of Kv1.1 and Kv 1.2, Two K Channel Proteinsm to Synaptic Terminals, Somata, and Dendrites in the Mouse Brain", *J. Neurosc.*, vol. 14, 1989, pp 360–368.

Wermelskirchen, et al., "Veratridine–Induced Intoxication: an In Vitro Model for the Characterization of Anti–Ischemic Compounds?", *Basic Clin. Physiol. Pharmacol.*, vol. 3, 1992, 293–321.

* cited by examiner

ID FOR PREVENTING AND
TREATING ARTHRITIS, OSTEO-
TRAUMATIC PAIN, AND NEURALGIAS
WITH TRIMEBUTINE

FIELD OF THE INVENTION

The field of the invention is related to methods for preventing and/or treating inflammatory somatic pain and chronic pain. More particularly the invention concerns the use of trimebutine [2-dimethylamino-2-phenylbutyl 3,4,5-trimethoxybenzoate hydrogen maleate] for preventing and/or treating inflammatory somatic pain as well as chronic pain.

BACKGROUND OF THE INVENTION

Trimebutine [2-dimethylamino-2-phenylbutyl 3,4,5- trimethoxybenzoate hydrogen maleate; TMB] has been used in many countries since 1969 for the treatment of functional bowel disorders, including irritable bowel syndrome (IBS). The efficacy of the compound to relieve abdominal pain has been demonstrated in various clinical studies using different protocols of treatment (Lüttecke, 1980; Moshal and Herron, 1979, Toussaint et al., 1981; Ghidini et al. 1986). Trimebutine was found to display weak agonist activity for rat brain and guinea-pig (Roman et al., 1987) or canine (Allescher et al., 1991) intestinal opioid receptors, without selectivity for any of the µ-, δ- and κ-subtypes. This weak activity was confirmed when using isolated intestinal fragments under transmural stimulation (Pascaud et al., 1987). This property could be responsible for the modulatory action of trimebutine on intestinal motility in fasted dog. Trimebutine given either intravenously or orally delays the appearance of a phase III of the migrating motor complex (MMC) in the stomach and the duodenum by inducing a premature phase III, migrating along the whole intestine (Bueno et al., 1987). In man, trimebutine stimulates intestinal motility in both fed and fasted states (Grandjouan et al., 1989). Furthermore, trimebutine reverses the effect of stress in jejunal motility (Delis et al., 1994).

More recently, trimebutine has been shown to be able to influence the activity of visceral afferents by decreasing the intensity of the recto-colonic reflex in rats as evidenced by the inhibition of colonic motility consecutive to rectal distension (Julia et al., 1996). This result may be related to the beneficial effects found with trimebutine in patients with IBS and more specifically in the treatment of attacks of abdominal pain.

There is a general agreement (9th World Congress on Pain, Vienna, August 1999) that there is an unmet medical need for the treatment of chronic pain. NSAIDs and opiates are ineffective in many cases. Antidepressants are being used with inconsistent eficacy (50–60%). Certain anticonvulsants (carbamazepine, clonazepam, baclofen) may be active. In extreme cases, capsaicin and local anesthetics are being tried. However, none of these approaches is satisfactory and some patients are refractory to all of them. In some cases like trigeminal neuralgia, neurosurgery (differential thermocoagulation of Gasser ganglion) remains the only way of alleviating pain.

From a starting point in visceral pain, the inventors found, as confirmed in the present application, that trimebutine has an inhibitory action on glutamate release through the blockade of sodium channels. More particularly, they found that the inhibition of glutamate release follows a presynaptic mechanism of action even though the opioid properties of trimebutine are not involved in this mechanism. In addition, as shown through results obtained in certain in vivo models and more particularly in models of hyperalgesia and chronic pain, they demonstrate that trimebutine can have an action on pain conditions other than visceral pain. This confirmes that trimebutine is useful in the treatment and/or the prevention of hyperalgesia and chronic pain as well as inflammatory somatic pain.

SUMMARY OF THE INVENTION

The invention relates to the use of trimebutine [2-dimethylamino-2-phenylbutyl-3,4,5-trimethoxybenzoate hydrogen maleate] or its corresponding stereoisomers for the preparation of a medicament to prevent and/or treat inflammatory somatic pain and chronic pain. For the present invention, trimebutine is administered orally or by injection and preferably by intravenous injection at a dosage between 50 to 900 mg/day (patient with average weight of 70 kg) and preferentially between 300 to 600 mg/day. Particular embodiments of the invention provide the use of trimebutine or its stereoisomers for the preparation of medicaments useful for preventing and/or treating inflammatory somatic pain (for example arthritis, polyarthritis, spondylarthritis) and chronic pain conditions (for example neurological pain, osteo-traumatic pain, back pain, cancer pain, neuralgias including post-zosterian neuralgia). Specific embodiments concern a method for preventing and/or treating inflammatory somatic pain and/or chronic pain comprising administering trimebutine to a patient in need thereof

DETAILED DESCRIPTION OF THE INVENTION

Figure 1:
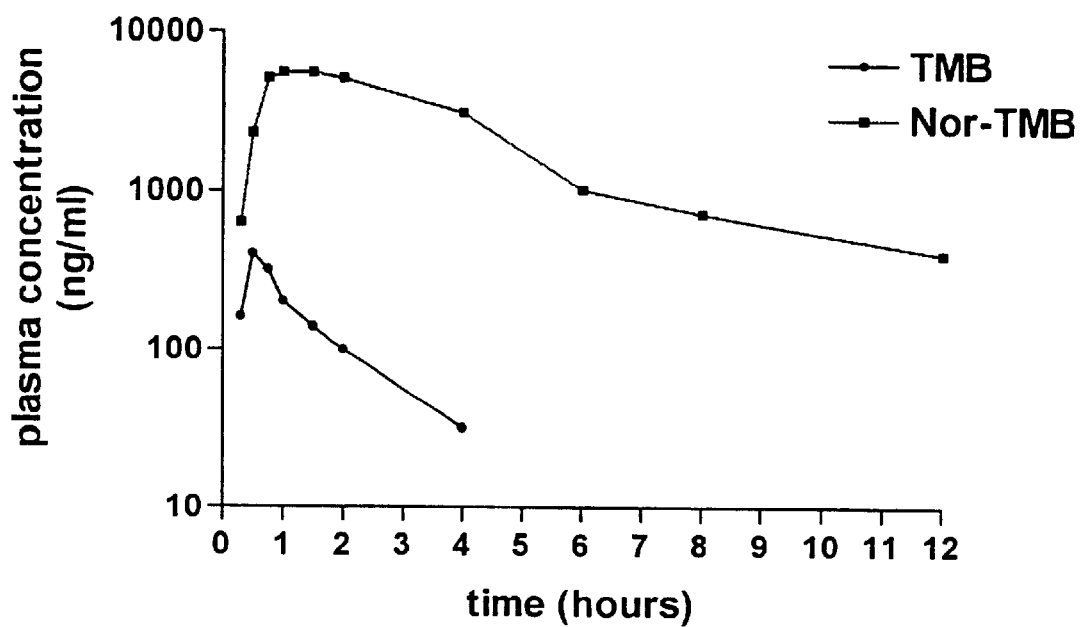
FIG. 1: Plasma concentrations of trimebutine (TMB) and N-desmethyl trimebutine (Nor-TMB) after oral administration of 900 mg of trimebutine.

As mentionned previously, the present invention stems from an unmet need in efficient treatment of inflammatory somatic pain as well as chronic pain. The pivotal role of glutamate and excitotoxic amino-acids (EAA) in the establishment of hyperalgesic or allodynic conditions has been evidenced by Dickenson et al., 1995. From that discovery, strategies have been set up for finding new analgesic drugs based on the inhibition of glutamate and EAA receptors. Most of the inhibitors that this strategy has generated cannot be used in human for safety reasons and it appears now that the blockade of glutamate receptors is a difficult way for drug discovery. The inhibition of glutamate release from presynaptic terminals as disclosed in the present invention, represents a more interesting strategy because the objective here is not blocking glutamate receptors that are involved in fundamental central nervous system transmission systems. Rather, by administration of compounds such as those disclosed in the instant application and which are able to inhibit glutamate release and to limit its access to the postsynaptic EAA receptors, it will be possible to modulate the hyperstimulation of EAA receptors and to avoid the installation of an hyperalgesic state resulting from the wind-up phenomenon observed in inflammatory injury. In the case of chronic pain conditions where the allodynic state is established, reduction of glutamate release in the synaptic cleft by action of these compounds will limit the activation of EAA receptors and will have an immediate effect on pain transmission circuitry.

The present invention thus provides methods for preventing and/or treating inflammatory somatic pain and chronic pain. More particularly the invention concerns the use of trimebutine [2-dimethylamino-2-phenylbutyl 3,4,5-trimethoxybenzoate hydrogen maleate] for preventing and/or treating inflammatory somatic pain as well as chronic pain.

Trimebutine (2-dimethylamino-2-phenylbutyl 3,4,5-trimethoxybenzoate hydrogen maleate, TMB) has been demonstrated to be active for relieving abdominal pain in humans. Interestingly, the inventors have now established that trimebutine and also some of its metabolites and preferably those called Nor-TMB hereafter (and preferably the (S)-enantiomer) which are major metabolites in humans, inhibit glutamate release from rat spinal cord slices, through the blockage of sodium channels according to a presynaptic mecanism. Furthermore, the results reported in the examples demonstrate that trimebutine, its stereoisomers and its metabolites have inhibitory effects on inflammatory somatic pain and chronic pain. It is understood that N-desmethyl trimebutine (Nor-TMB) comprises the compounds (S)-N-desmethyl trimebutine, (R) N-desmethyl trimebutine and the racemate. In addition, it is known that in humans, after oral or iv administration of trimebutine, this latter serves as a metabolic precursor for N-desmethyl trimebutine (Nor-TMB). In volunteers given tablets of 900 mg of trimebutine, N-desmethyl trimebutine is found as being the most important compound in plasma: 1 hour after oral administration, when plasma concentrations of TMB are maximal, maximal plasma concentrations of Nor-TMB are about 15 fold higher. This indicates that trimebutine is acting like a bioprecursor of Nor-TMB meaning that under action of hepatic enzymes, the bioprecursor trimebutine is metabolized and gives rise to a new molecule. In this respect, any data contributing to the pharmacological characterization of Nor-TMB is useful for the understanding and the description of the effects of trimebutine. Indeed, the administration of trimebutine in humans leads to the concomitant exposure to trimebutine, Nor-TMB and other metabolites. Therefore these compounds and particularly trimebutine and Nor-TMB are able to elicit jointly their antinociceptive properties. Accordingly, trimebutine and trimebutine-related molecules including Nor-TMB have been shown by the inventors to be able to display antinociceptive properties in various models of inflammatory and/or chronic pain. The inventors thus have demonstrated that trimebutine, its stereoisomers and also its metabolites have an inhibitory action on inflammatory somatic pain and on chronic pain installation by inhibiting glutamate release, an effect due to the blocking activity of these compounds on sodium channels.

Especially, trimebutine, its stereoisomers, and Nor-TMB have been studied for their affinity towards sodium channels labeled by [$^3$H]-batrachotoxin, their effect on sodium, potassium and calcium currents in rat dorsal root ganglia neurons, on veratridine-induced glutamate release from rat spinal cord slices. Trimebutine and Nor-TMB have been evaluated in four models of inflammatory or chronic pain: formalin induced pain in rat, PGE$_2$ induced hyperalgesia in rat, in a rat model of mononeuropathy and in a rat model of chronic pain induced by streptozocin-induced diabetes. Results of these experiments demonstrate that trimebutine and Nor-TMB are able to block sodium channels and veratridine-induced glutamate release from rat spinal cord slices. In addition, trimebutine and Nor-TMB display an analgesic activity.

Accordingly, the present invention relates to the use of trimebutine [2-dimethylamino-2-phenylbutyl-3,4,5-trimethoxy-benzoate hydrogen maleate] or its corresponding stereoisomers for the preparation of a medicament to prevent and/or treat inflammatory somatic pain and chronic pain. It should be understood by inflammatory somatic pain, any pain other than visceral pain involving an inflammatory process such as arthritis, polyarthritis, spondylarthritis. In addition, the invention concerns the use of trimebutine or its corresponding stereoisomers for the preparation of a medicament to prevent and/or treat chronic pain. Chronic pain, according to the definition proposed by the International Association for the Study of Pain, is a pain which persists beyond normal tissue healing time (suggested three months: International Association for the Study of Pain, Classification of chronic pain. Pain, 1986, Suppl 3, S1-S226), and this implies a transition point from acute pain. Accordingly and since chronic pain results from hyperalgesia (Dickenson et al., 1995), one embodiment of the present invention is the prevention and/or treatment of hyperalgesia or pain related to central hypersensitivity conditions. In hence, the present invention is particularly useful for preventing and/or treating:

Neurological pain such as neuropathies, polyneuropathies including those related to diabetes, headache, trauma, neuralgias including post-zosterian neuralgia and trigeminal neuralgia, algodystrophy, HIV related pain, Musculo-squeletal pain such as osteo-traumatic pain, arthritis, osteoarthritis, spondylarthritis as well as phantom limb pain, back pain, vertebral pain, shipped disc surgery failure, post-surgery pain, Cancer related pain, Vascular pain such as pain resulting from Raynaud's syndrome, Horton's disease, arteritis, varicose ulcers.

In the context of the present invention, trimebutine is provided in a pharmaceutical composition for preventing and/or treating the above mentioned pains. Pharmaceutical compositions include trimebutine and/or its corresponding stereoisomers including their salts and is produced by formulating the active compound in dosage unit form with at least one solid or liquid pharmaceutical acceptable carrier or excipient. Where it is appropriate to form a salt, the pharmaceutically acceptable salts include acetate, benzenesulfonate, benzoate, bitartrate, calcium acetate, camsylate, carbonate, citrate, edetate, edisylate, estolate, esylate, fumarate, gluceptate, gluconate, glutamate, glycoloylarsanilate, hexylresorcinate, hydrabamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate or hemi-tartrate, theoclate, triethiodide, benzathine, chloroprocaine, choline, diethanolamine, ethylenediamine, meglumine, procaine, aluminum, ammonium, tetramethyl ammonium, calcium, lithium, magnesium, potassium, sodium, and zinc. (See also "Pharmaceutical salts" by Berge S. M. et al. (1997) *J. Pharm. Sci.* 66: 1–19, which is incorporated herein by reference.)

Solid dosage forms for oral administration include capsules, tablets, pills, powders, and granules. In such solid dosage forms, the active component is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose as well as high molecular weight polyethyleneglycols, and the like.

Solid dosage forms such as tablets, dragées, capsules, pills, and granules can be prepared with coatings and shells, such as enteric coatings and others well known in the art. The active component can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to trimebutine, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, and the like. Suspensions, in addition to trimebutine, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions suitable for parenteral injection may comprise physiologically acceptable sterile aqueous or non aqueous solutions, dispersions, suspensions or emulsions, and sterile powders for reconstitution into sterile injectable solutions or dispersions. Examples of suitable liquid carriers, diluents, solvents or vehicles include water, ethanol, polyols (propyleneglycol, polyethyleneglycol, glycerol, and the like), and suitable mixtures thereof.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Preferably the composition is in unit dosage form. In such form, the preparation is divided into unit doses containing appropriate quantities of trimebutine. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms. Some examples of dosage unit forms are tablets, capsules, pills, powders, suppositories, aqueous and non aqueous oral solutions and suspensions, and parenteral solutions packaged in containers containing either one or some larger number of dosage units and capable of being subdivided into individual doses.

Accordingly, trimebutine or its corresponding stereoisimers are administered at a dosage between 50 to 900 mg/day (patient with an average weight of 70 kg) and preferentially between 300 to 600 mg/day. The term "patient" is intended to include any mammal and especially human whom the trimebutine is administred. Routes of administration are preferably the oral and the parenteral routes and especially the injection routes and particularly the intravenous injection route. However, any compatible route such as subcutaneous, intramuscular, intrathecal, intraperitoneal routes can also be considered in the context of the present invention.

Another embodiment of the invention is related to a method for preventing and/or treating inflammatory somatic pain comprising administering trimebutine to a patient in need thereof. The present invention provides also a method for preventing and/or treating chronic pain comprising administering trimebutine to a patient in need thereof. The meaning of the terms "somatic" or "chronic" pain is the same as defined above as well as "patient". The biochemical and pharmacological data reported in the examples allow a better understanding of the mechanism of action of trimebutine. They support the assumption that, besides its regulatory effects on colonic motility already reported in the past and which had been related to its weak opioid properties, trimebutine is endowed with antinociceptive properties which are due to its blocking effect on $Na^+$ channels. These new properties of TMB explain how this compound is a useful method for preventing and/or treating inflammatory somatic pain and/or chronic pain.

The present invention will be further disclosed in the following examples without limiting the scope of the invention.

EXAMPLES

Material and Methods

Animals

Male Sprague-Dawley rats (IFFA Credo, Saint Germain sur l'Arbresle, France), weighing 225–250 g ([$^3$H]-batrachotoxin binding experiments) or 350–375 g (glutamate release experiments), or pregnant rats (electrophysiological experiments) are used in this experiment and are cared for in accordance with the institutional guidelines for animal welfare: temperature 21±3° C.; light/dark: 12 h/12 h.

Drugs and Media

Trimebutine maleate, (S)-Trimebutine, (R)-Trimebutine, are are synthetized according to the process disclosed in the french patent FR 2,369M (1962) and the japanese patent application published under n° 16416 (1980) and incorporated herein by reference. Flunarizine, L-glutamatic acid, lidocaine hydrochloride, bupivacaine, trypsin and DMEM-F12 are purchased from Sigma (St Quentin Fallavier, France), morphine from Francopia (Gentilly, France), veratridine from RBI, Bioblock Scientific (Illkirch, France), gentamicine from Boehringer Mannheim S. A. (Meylan, France). All reagents used for the preparation of buffers and solutions are of analytical grade from Merck (Merck-Clevenot, Nogent sur Marne, France). (S)-N-desmethyl-TMB maleate is synthetized according to the process disclosed in WO 99/01417 and incorporated herein by reference. L-[G-$^3$H]-glutamic acid (49 Ci/mmole), is from Amersham (Les Ulis, France). Dulbecco's modified Eagle medium, Neurobasal medium, fetal calf serum were from Gibco, Life Technologies S.A.R.L. (Cergy Pontoise, France). Horse serum is from Seromed, (Berlin, Germany).

Example 1

[$^3$H]-batrachotoxin Binding

The purpose of the present example is to determine the affinity of the tested compounds to [$^3$H]-batrachotoxin binding sites in rat cortical synaptosomes, representing site 2 of the sodium channel 1.1 Material and Methods a) Synaptosomal Membranes Cerebral cortices from male Sprague-Dawley rats are homogenized in a glass-Teflon homogenizer in 10 volumes of ice-cold 0.32 M sucrose, 5 mM $K_2HPO_4$ (pH 7.4 at 4° C.). The homogenate is centrifuged at 1000 g for 10 min; the new pellet is resuspended in the same volume of sucrose and recentrifuged. The new pellet is discarded and the two supernatants resulting from these two centrifugations are pooled and centrifuged at 20,000 g for 10 min. The resulting pellet is resuspended in a sodium-free assay buffer containing 50 mM HEPES (N-2-hydroxyethylpiperazine-N'-2-ethanesulphonic acid), 5.4 mM KCl, 0.8 mM $MgSO_4$, 5.5 mM glucose and 130 mM choline chloride (pH 7.4 at 25° C.).

b) Binding Experiment

Binding assays are initiated by the addition of 150–200 μg synaptosomal protein to an assay buffer containing 25 μg scorpion venom (*Leireus quinquestriatus*), 0.1% BSA, 10 nM [$^3$H]-batrachotoxin and various concentrations of test drugs (250 μl final volume). Non-specific binding is determined in the presence of 0.3 mM veratridine. Reactions are incubated for 90 min at 25° C. and the bound ligand is separated from the free by vacuum filtration through GF/B filters (Filtermate, Packard). The filters are washed with 2×5 ml buffer (5 mM HEPES, 1.8 mM $CaCl_2$, 0.8 mM $MgSO_4$, 130 mM choline chloride, 0.01% BSA; pH 7.4 at 25° C.) and bound ligand is estimated by using liquid scintillation spectrometry (Topcount, Packard).

c) Calculations

In all experiments examining the displacement of [$^3$H]-batrachotoxin binding by unlabeled drugs, concentration-response curves are generated using six concentrations of drugs. All assays are performed at least three times, with each determination performed in duplicate. Data are expressed as mean values±SEM of at least three determinations. Displacement curves are fits generated by Graph-Pad Software. Displacement plots are analysed by a non linear regression analysis using the LIGAND computer program (Mc Pherson, 1985). These analysis generated Hill coefficient ($n_H$) and $IC_{50}$ values. Ki values are calculated from $IC_{50}$ values using the Cheng-Prusoff (1973) relationship.

1.2 Results

Figure 2:
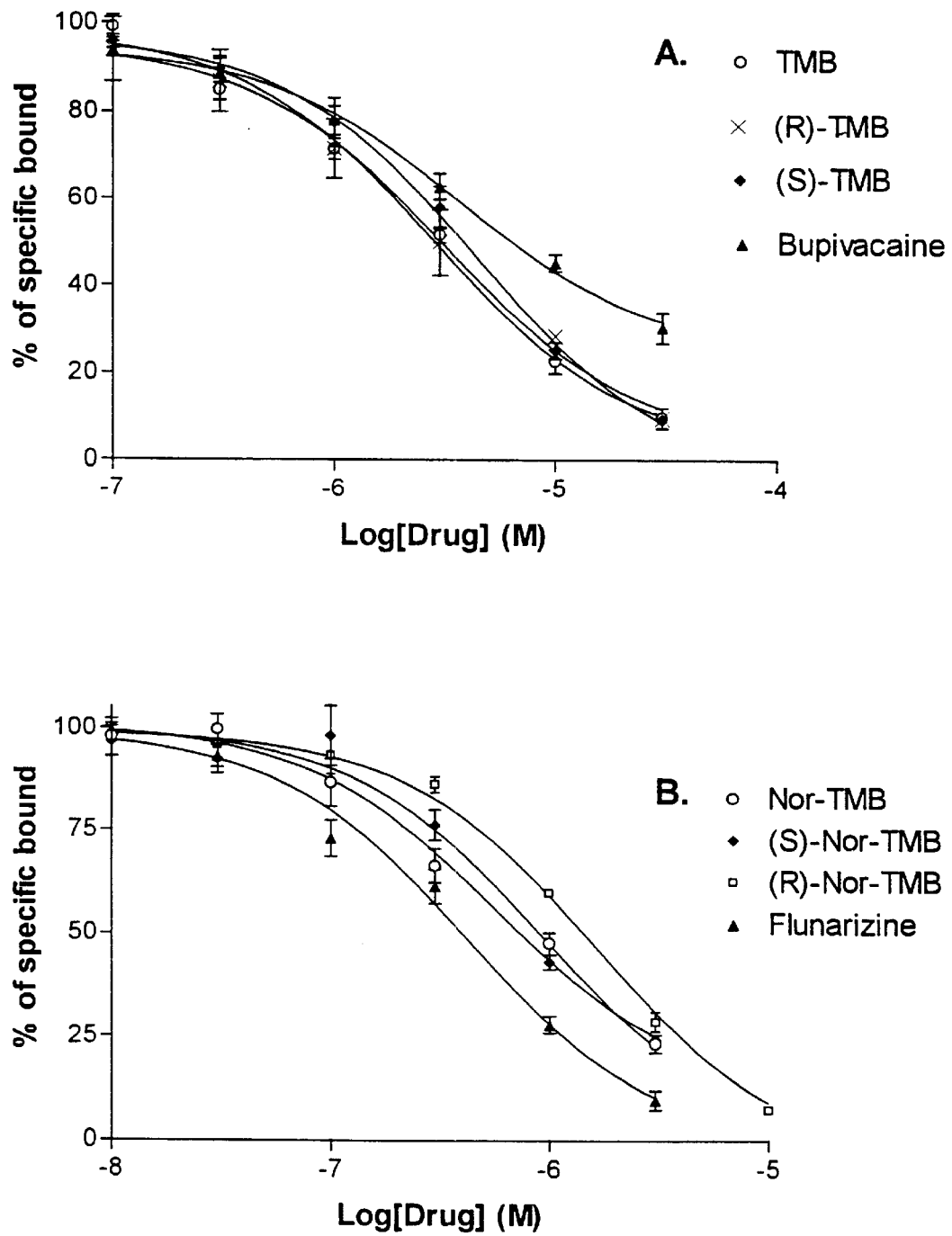
FIGS. 2(A and B): Effect of TMB (A), Nor-TMB (B) and their corresponding stereoisomers on [$^3$H]-batrachotoxin binding to rat cortical synaptosomes. Membranes are incubated with increasing concentrations of test drugs in presence of 25 µg scorpion venom and 10 nM [$^3$H]-batrachotoxin. Non specific binding is determined in the presence of 0.3 mM veratridine. After 90 min incubation at 25° C., bound ligand is separated from free ligand by vacuum filtration through GF/B filters. Specific binding in presence of test compounds is calculated as percentage of control binding determined in absence of inhibitors. Represented values are mean±SEM from at least 3 independent determinations performed in duplicate.

The results presented in FIGS. 2(A) and (B) show that trimebutine, its stereoisomers and its metabolites displace [$^3$H]-batrachotoxin from its binding sites to rat cortical synaptosomes with potencies lying between that of bupivacaine (Ki=7.14±0.96 μM) and that of flunarizine (Ki=0.38±0.05 μM). For all compounds, the displacement of [3H]-batrachotoxin is complete and the calculated Hill coefficient is close to 1 (FIG. 2). The affinity of trimebutine is found with Ki=2.66±0.15 μM. For this compound, no stereoselectivity is evident since the corresponding stereoisomers display affinities similar to that of racemates. The values for the (S) and (R) enantiomers are: Ki=3.31±0.36 μM and Ki=2.89±0.88 μM respectively. For Nor-TMB, the values for the (S) and (R) enantiomers are: Ki=0.80±0.04 μM and Ki=1.26±0.07 μM, respectively.

Hence, the present example demonstrates that trimebutine, its stereoisomers and Nor-TMB display affinity for [$^3$H]-batrachotoxin binding sites in the same order of magnitude than bupivacaine or flunarizine, two sodium channel blockers.

Example 2

[$^3$H]-glutamate Release

The purpose of the present example is to determine the ability of trimebutine and its metabolites to inhibit the release of glutamate from rat spinal cord slices. This example shows that trimebutine, its metabolites and their corresponding stereoisomers inhibit veratridine-induced glutamate release in vitro. Veratridine is known to induce glutamate release by activating voltage-dependent $Na^+$ channels, resulting in $Na^+$ influx with consecutive reduction of the transmembrane gradient (Wermelskirchen et al., 1992).

2.1 Material and Methods a) Buffers

Two buffers are prepared: an incorporation buffer (modified Krebs solution: 119 mM NaCl, 5 mM KCl, 0.75 mM $CaCl_2$, 1.2 mM $MgSO_4$, 1 mM $NaH_2PO_4$, 25 mM HEPES, 1 mM $NaHCO_3$, 11 mM D-glucose, 67 $\mu$M EDTA, 1.1 mM L-ascorbic acid (pH 7.4) gassed with 95% $O_2$ and 5% $CO_2$) and a superfusion buffer identical to the incorporation buffer except that EDTA and ascorbic acid are omitted. Compounds to be tested and veratridine are diluted in this superfusion buffer.

b) Rat Spinal Cord Slices

After decapitation of animals, a 1.5 cm segment of lumbar spinal cord is isolated after a lumbosacral laminectomy and submerged in a ice-cold modified Krebs solution gassed with 95% $O_2$ and 5% $CO_2$. After removal of the dura matter, all ventral and dorsal roots are cut at the root of the entry zone. Slices (250 $\mu$m thick cube-like blocks) are prepared using three successive sections performed with McIllwain tissue chopper.

c) Superfusion Experiments

Slices are incubated for 5 min at 30° C. in 5 ml of incorporation buffer maintened under oxygenation and containing 10 $\mu$M L-glutamic acid and 4 $\mu$Ci/ml [$^3$H]-glutamic acid. After incubation, the slices are transferred into superfusion chambers in an automatic superfusion apparatus (Brandel). The apparatus consists in a device of 20 chambers allowing to run simultaneously 20 experiments and to control the sequence of buffers used in the superfusion by programming of an Apple IIe computer. This system makes it possible to test various experimental groups in the same run (4 groups of 5 chambers). After a washout period of 45 min, at a flow rate of 0.5 ml/min, veratridine (40 $\mu$M) is added for 5 min to the superfusion medium. When drugs are tested (trimebutine and its stereoisomers), they are added to the superfusion medium 15 min before and also during veratridine application. Fractions of superfusate corresponding to 5 min are collected during the 30 min following the stimulation. At the end of the run, the slices are removed from the chambers and 2.5 ml of scintillation liquid (Hionic Fluor, Packard ) are added to the slices and to each of the fractions. The radioactivity is determined using liquid scintillation spectroscopy (Minaxi, Packard). The efflux of radioactivity is assumed to be due mainly to [$^3$H]-glutamate efflux (Turner and Dunlap, 1989).

d) Data Analysis

All values are expressed as the mean±SEM of at least 5 determinations. Release of radioactivity for each fraction is expressed in terms of fractional release calculated by dividing the radioactivity in each fraction by the amount remaining in the filter. The stimulation produced by veratridine is quantified by cumulating the release of radioactivity measured in the fractions collected after the stimulation. The effect of tested compounds is evaluated as percent of inhibition by comparing the total amounts of radioactivity released in control chambers to those released in chambers superfused with test compounds. From these percent inhibitions, $IC_{50}$ values are calculated by plotting probit values of inhibition versus log values of concentrations. Statistical analyses are performed using Student's unpaired two tailed t-test. Statistical differences are considered significant at $P<0.05$.

2.2 Results

Figure 3A:
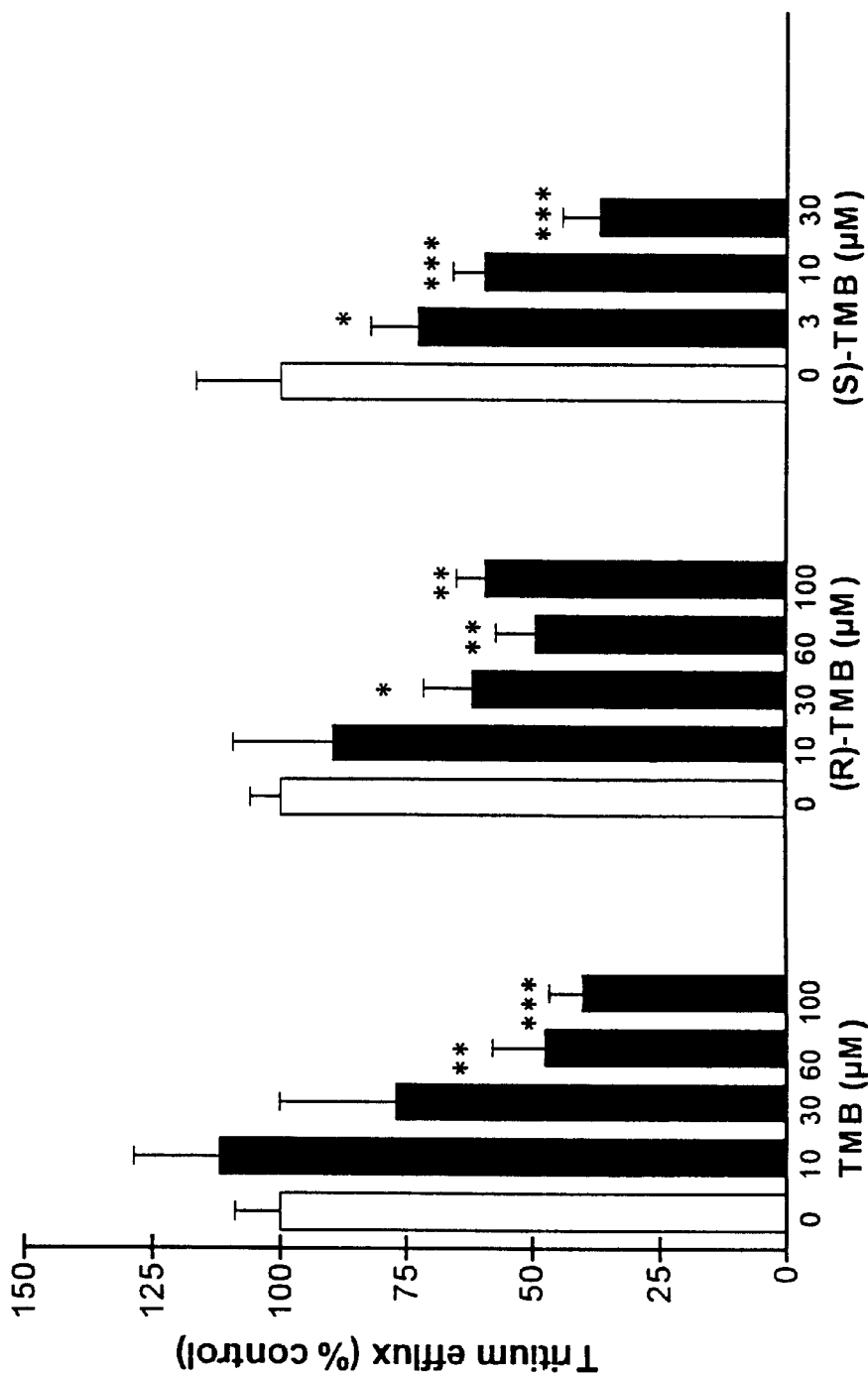
FIGS. 3A, 3B, and 3C: Effect of TMB (A), Nor-TMB (B) and their corresponding stereoisomers, on veratridine-induced glutamate release from rat spinal cord slices. Morphine and bupivacaine (C) are tested in the same condition. Results are means±SEM of at least 10 determinations. The slices are superfused 15 min with the test compound prior to stimulation with veratridine (40 µM). The radioactivity collected in 5 min fractions during 30 min after the stimulation is counted and the effect of compound is determined by comparing the cumulated quantity of radioactivity released to that obtained in cells superfused with buffer alone.*P<0.05; P<0.01;*P<0.001, Student's test.
Figure 3B:
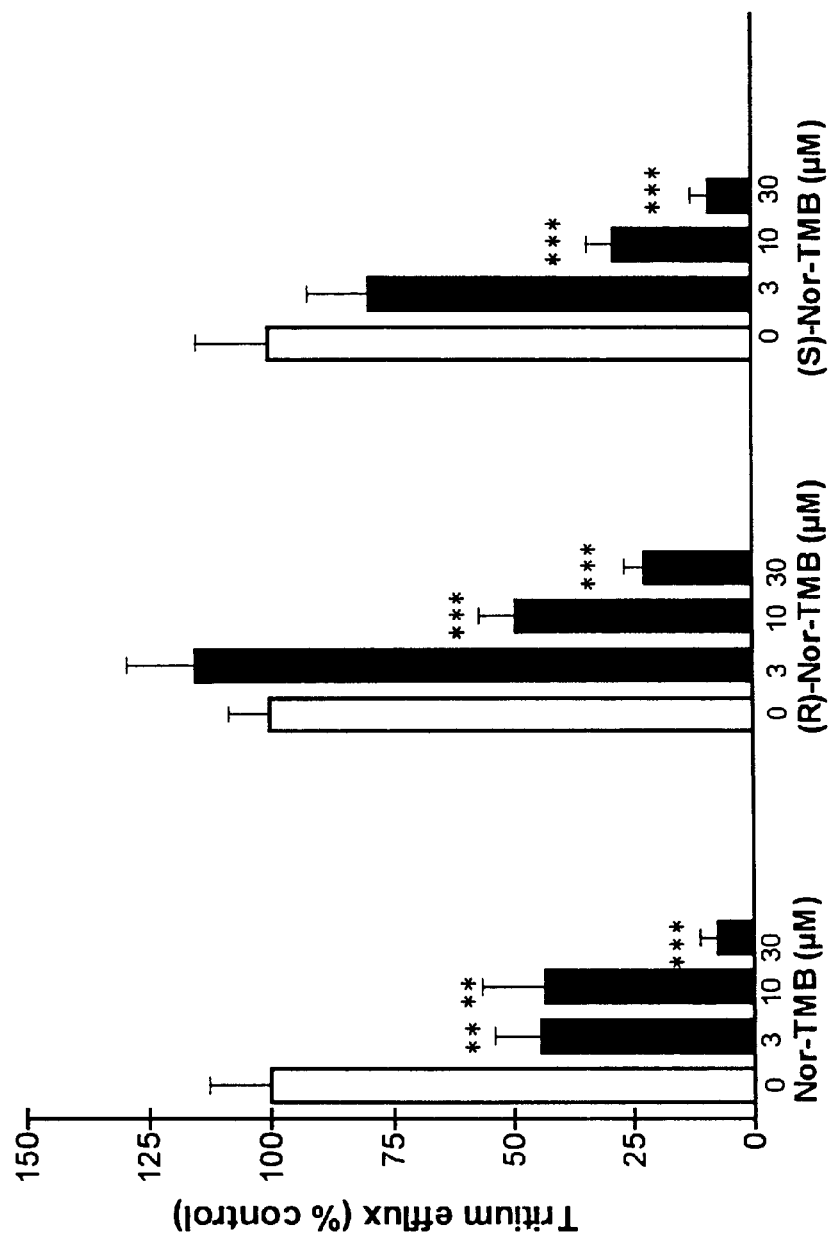
Figure 3C:
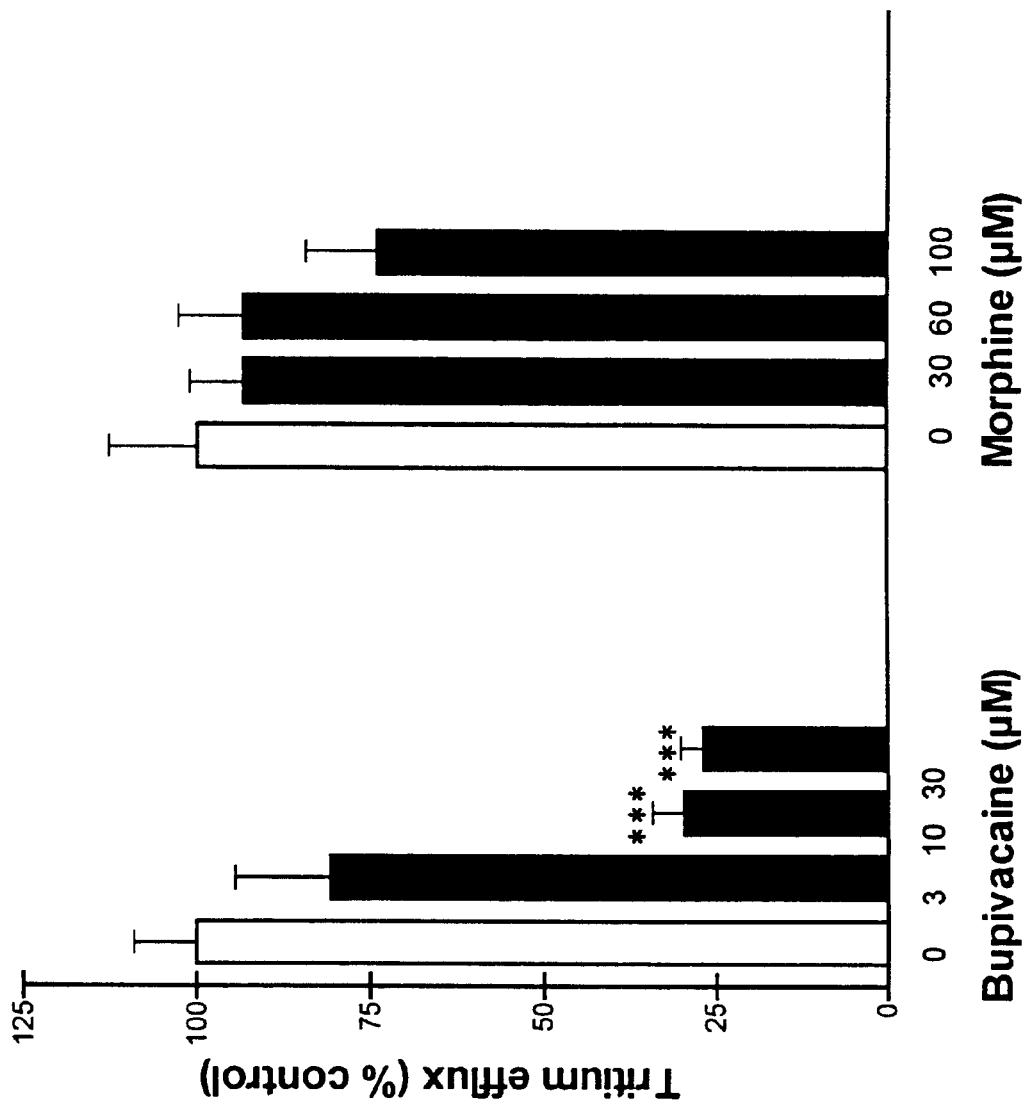

The results presented in FIG. 3 demonstrate that trimebutine inhibits dose-dependently veratridine-induced glutamate release at concentrations higher than 60 mM (FIG. 3A). Furthermore, 50 to 60% inhibition could be reached at concentrations as high as 100 $\mu$M. (R)-trimebutine presents a profile similar to the racemate whereas (S)-trimebutine presents a significant inhibition from the concentration of 3 $\mu$M (FIG. 3A). The estimated $IC_{50}$ is 15.2 $\mu$M for (S)-trimebutine, whereas it could not be calculated ($IC_{50}>100$ $\mu$M) for trimebutine and (R)-trimebutine. For Nor-TMB and its stereoisomers (FIG. 3B), the inhibitory effect is significant (p<0.01) at 3, 10 and 30 $\mu$M and $IC_{50}$ value is 8.4 $\mu$M. (S)-Nor-TMB displays an activity ($IC_{50}$=6.3 $\mu$M) similar to that of the racemate and similar also to that of the second enantiomer (R)-Nor-TMB ($IC_{50}$=16.3 $\mu$M). These results are in agreement with results from other papers reporting that compounds that inactivate voltage-dependent $Na^+$ channels prevent veratridine-induced glutamate release in vitro and in vivo (Lees and Leach, 1993). In a similar manner, the effect of TMB and related compounds on veratridine-induced glutamate release is due to their blocking activities on sodium channels. When bupivacaine is evaluated under the same experimental conditions (FIG. 3C), an $IC_{50}$ value of 8.2 $\mu$M could be estimated. Morphine is found inactive in this paradigm up to 100 $\mu$M (FIG. 3C). The lack of effect of morphine in this model suggests that the effects of trimebutine on glutamate release are not due to the opioid properties of the compounds demonstrated in previous studies (Roman et al., 1987).

This result is quite important given the pivotal role of glutamate and excitatory amino acids (EAA) in the transmission of nociceptive message and more particularly in hyperalgesic conditions. In this respect, the finding that TMB and its metabolites are able to reduce the extracellular concentrations of glutamate by inhibiting its release from presynaptic pools represents an exciting property of TMB in its therapeutic use as analgesic agent.

Example 3

Electrophysiological Experiments

The purpose of this example is the study of the effects of trimebutine and its stereoisomers on sodium, potassium and calcium currents.

3.1 Material and Methods a) DRG Neurons

Experiments on sodium and calcium currents are performed using cultured rat dorsal root ganglia (DRG) excised from 14- to 15-day-old rat embryos. Methods for cell isolation and culture are derived from those described by Valmier et al. (1989). Pregnant Sprague-Dawley rats are killed by placing them in a $CO_2$ atmosphere for 5–6 min. Three to five embryos are removed aseptically and placed in a Petri dish containing the following B medium supplemented with antibiotics (streptomycin, 50 $\mu$g/ml; penicillin, 50 U/ml). The B medium contained (in mM): 137 NaCl, 5.4 KCl, 0.4 $Na_2HPO_4$, 0.8 $MgSO_4$, 0.8 $MgCl_2$, 1.8 $CaCl_2$, 6 glucose, 10 HEPES. The dorsal root ganglia are removed from the excised spinal cord and digested for 6 min in 2 ml of Dulbecco's modified Eagle medium containing 0.1% trypsin. Cells are dissociated mechanically through fire-polished Pasteur pipettes and plated in polyornithine-laminine coated dishes. The culture medium is the Neurobasal medium containing, 0.5 mM glutamine and 25 $\mu$M glutamate. The cells are incubated at 37° C. in 5% $CO_2$. Electrophysiological experiments are performed from 4–6 h to 24 h after plating.

b) Rat Pituitary Cell Line $GH_3/B_6$

This cell line, of rat pituitary origin, exhibits voltage-dependent calcium currents of low and high activation thresholds as well as TTX (tetrodotoxin)-sensitive sodium currents (Matteson and Armstong, 1984). Proliferating $GH_3$ cells are grown at 37° C. in a 5% $CO_2$ environment. The growth medium contained DMEM-F12 supplemented with 12.5% horse serum and 2.5% fetal calf serum. When the cells came to confluence, they are split and replated at $5 \times 10^4$ cells in 5 ml growth medium.

c) Potassium Channels Expressed in Xenopus Oocytes

Two voltage-dependent $K^+$ channels are considered: the shaker-related Kv1.1 and Kv1.2 channels. These channels are selected in view of their involvement in the central and peripheral nervous system, particularly at nerve endings and Ranvier nodes of myelinated fibres (Wang et al., 1994). The rat voltage-dependent rKv1.1 and rKv1.2 channels are expressed in Xenopus oocytes. The rKv1.1 and rKv1.2 cDNAs are a generous gift from S. Alper (Beth Israël Hospital, Havard Medical School, Boston Mass., USA). The transcriptions are done using the Ambion Megascript (Ambion, USA) and the cRNAs are stored in water at 1 mg/ml. cRNAs injection in Xenopus oocytes is done at 2–4 ng/ml. Defolliculated oocytes are kept in ND96 medium supplemented with 0.1 U/ml gentamicin. The currents are recorded 1–6 days after injection.

d) Electrophysiology

Conventional whole cell patch clamp experiments are performed at room temperature using an EPC7 (List) patch clamp amplifier. CH3/B6 cells and DRG neurons are bathed in a Hanks derived medium containing (in mM): 143 NaCl; 10 $CaCl_2$; 5.6 KCl, 2 $MgCl_2$, 5 glucose and 10 HEPES, pH adjusted to 7.4 with NaOH (osmolarity, 300–310 mosm/l). Calcium currents are recorded in the presence of $10^{-5}$M TTX and 10 mM TEA (tetraethylammonium). For recording sodium current, calcium is replaced by $Mg^{2+}$ in the presence of 10 mM TEA. Patch electrodes used for recording $Na^+$ and $Ca^{2+}$ currents are filled with the following saline (in mM): 140 CsCl, 1.1 EGTA (ethyleneglycol-bis (β-aminoethyl ether) N,N,N',N'-tetraacetic acid), 5 HEPES, 2 $MgCl_2$, pH ajusted to 7.2–7.3 with CsOH (osmolarity, 290 mosm/l). The electrodes are pulled in 4 steps from 1.5 mM glass capillaries (GC 150 TF, Clark Electromedical Instruments) using a P87 puller (Sutter Instruments) and fire-polished. The tip resistance is 2–3 MΩ.

Drugs are dissolved in the bath medium (from stock solutions at $10^{-2}$ M in DMSO (dimethylsulfoxide)) and applied by pressure ejection (Pneumatic Picopump PV820, WPI) from glass pipettes (10–20 μm tip diameter) located at 50–60 μm from the recorded cell. A two-electrode voltage clamp amplifier (Geneclamp 500, Axon Instruments) is used to record $K^+$ currents from Xenopus oocytes. The KCl (3M)-filled electrodes had tip resistance<1 MΩ. The oocytes are continuously superfused with a $Ca^{2+}$-free ND96 medium in order to abolish the large $Ca^{2+}$-activated $Cl^-$ current present in these cells.

e) Calculations

Data are sampled at 2 kHz. Software for stimulation, acquisition and analysis is constructed in house. The dose-response curves are constructed with various drug concentrations separated by wash periods. Each point is the mean±SEM of 3 to 6 experiments. Experimental points are fitted to the theoretical Hill curve using the least-square Minsq program: $y=1/(1+[X]^n/IC_{50}^n)$ in which y is the fraction of $Na^+$ current persisting in the presence of the drug applied at the concentration [X], $IC_{50}$ is the concentration of drug that half-blocks the $Na^+$ current, and n is the Hill coefficient corresponding to the number of drugs required to block one $Na^+$ channel.

3.2 Results a) Sodium Currents

Figure 4:
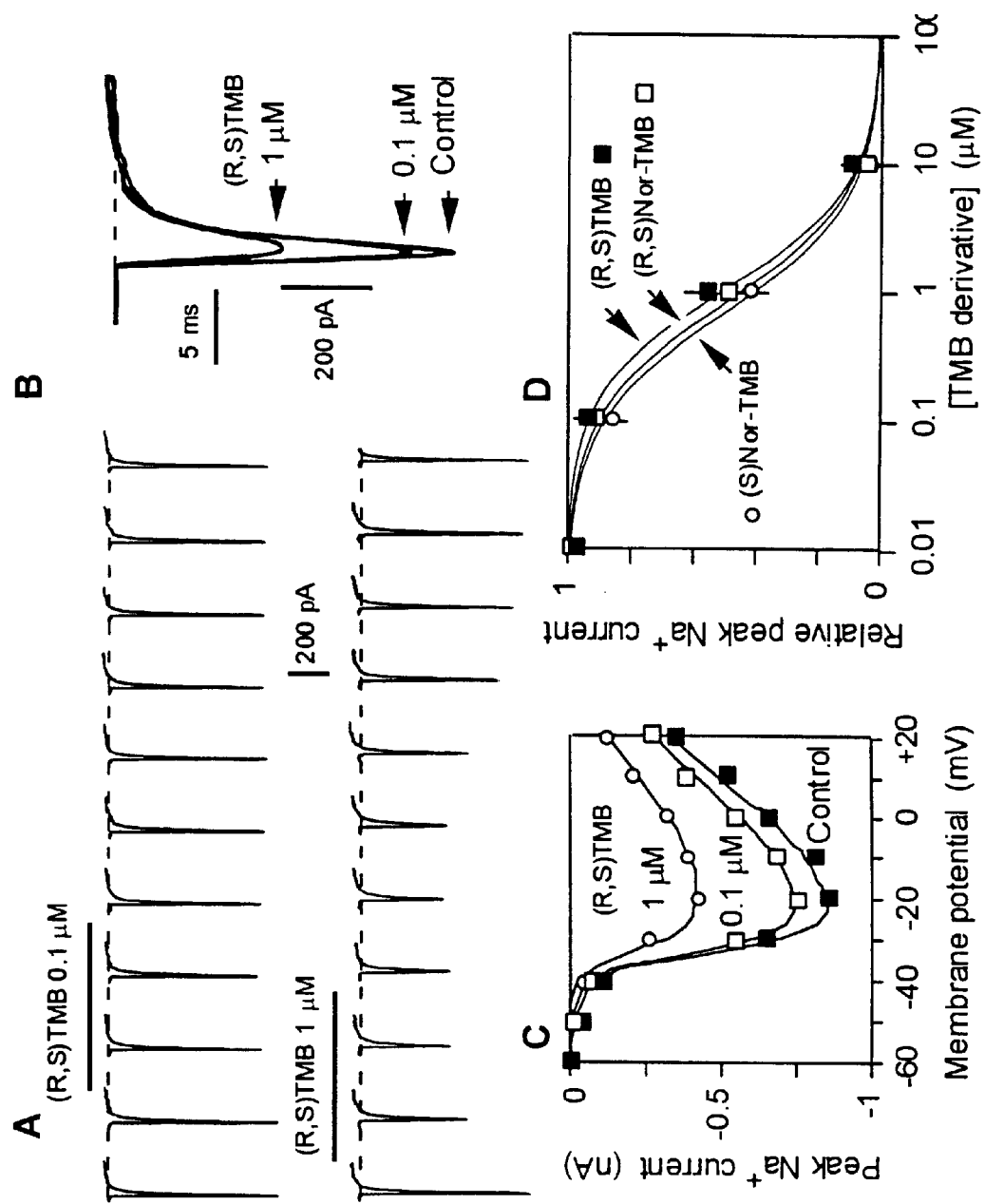
FIGS. 4(A, B, C, and D): Effect of TMB on sodium currents measured in DRG neurons. (A) Inward Na$^+$ current induced every 10 s by stepping the membrane potential from −80 to −10 mV. TMB is locally applied for 20 s at 0.1 µM (top row) and at 1 µM (bottom row). (B) Sodium current before (control) and during TMB perfusion (same cell as in A.). (C) Peak sodium current versus pulse potential in control saline and in the presence of TMB at the concentrations indicated. The decrease in peak sodium current occurred homothetically. (D) Dose-response relationship of TMB effects on DRG Na$^+$ current. Results are expressed as the Na$^+$ current part (relative peak Na$^+$ current) persisting in the presence of the blocker. Each point is mean± S.E.M. of 4 to 6 experiments. Continuous curve: best fit to Hill function with IC$_{50}$=0.69 µM, and n$_H$=1.02.

In FIG. 4A are shown the effects of the successive 20s applications of trimebutine at 0.1 and 1 μM on the sodium current of a DRG neuron. In this representative experiment, TMB induced a reversible blockade of the current amounting to 13% and 61% at 0.1 and 1 μM respectively. The blockade occurred without any evidence of changes in current kinetic (FIG. 4B) and voltage dependence (FIG. 4C). The dose-response curve obtained by applying 0.01, 0.1, 1 and 10 μM trimebutine is shown in FIG. 4(D) as a plot of the current part remaining in the presence of the blocker. The inhibition parameters calculated from this curve are: $IC_{50}$= 1.05±0.09 and $n_H$=1.09±0.10. The parameters calculated for Nor-TMB are very similar.

A kinetic study is performed using (R,S)-TMB. The unblocking rate $k_{off}$ is determined from the time constant $\tau_{off}$=34±4 s (n=6) of the exponential recovery from block: $k_{off}=1/\tau_{off}=29 \cdot 10^{-3}$ $s^{-1}$.

The blocking rate $k_{on}$ is deduced from $K_D=k_{off}/k_{on}$; $k_{on}$= 35–40 $10^{-3}$ $s^{-1}$. These reaction rates defined the 3 drugs as fast $Na^+$ channel blockers; for instance, 10 μM (R,S)-TMB blocked the channels with a time constant of 2.2 s.

b) Calcium Currents

Figure 5:
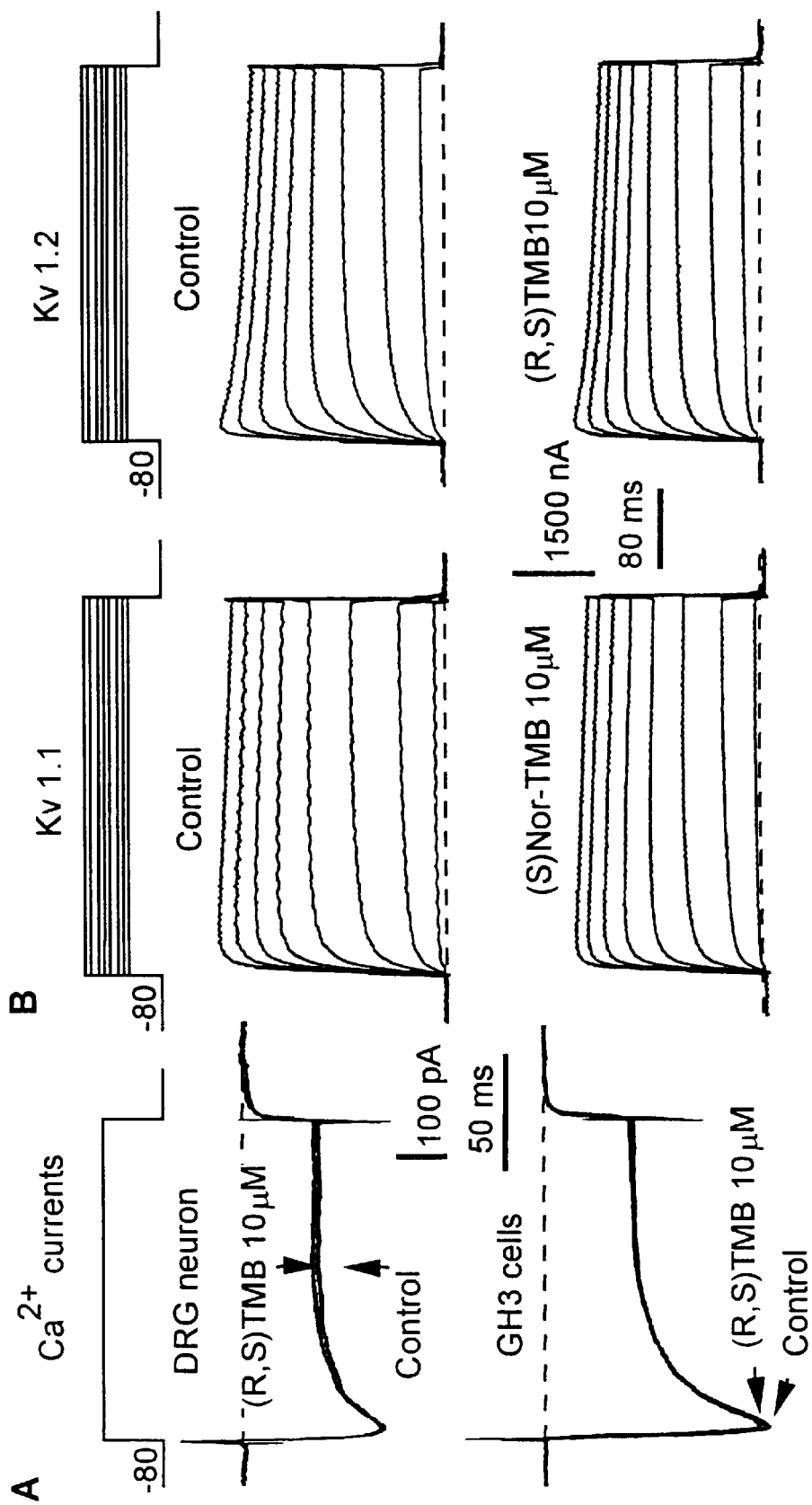
FIGS. 5(A and B): Effect of TMB on voltage-dependent calcium and potassium currents. (A) Calcium currents from DRG neurons and GH$_3$ cells. Currents induced by 150 ms depolarization from −80 to −10 mV. (B) Potassium currents expressed in Xenopus oocytes. Superimposed current traces induced by 400 ms depolarizations at −40 to +20 mV (in 10 mV step from −80 mV).

In both GH3 cells and DRG neurons, the three drugs applied at 10 μM had no significant effects on either the low threshold transient T-type $Ca^{2+}$ currents (early peak in FIG. 5A) or the high threshold slowly inactivating $Ca^{2+}$ currents (steady state inward current in FIG. 5A).

c) Potassium Currents

Tests are performed on the voltage-dependent Kv1.1 and Kv1.2 channels expressed in Xenopus oocytes. The three drugs applied at 10 μM had a slight depressing effect on the three $K^+$ currents (mean block: 12±4%, n=18), the most effective compound in this respect being (R,S)-TMB (23±6% current block; FIG. 5B). This effect occurred without obvious changes in the cell resting potential and input resistance. These electrophysiological data confirm the results on [$^3$H]-batrachotoxin binding (example 1) and glutamate release (example 2) by demonstrating that TMB and its stereoisomers block reversibly the sodium currents in DRG neurons and also in GH3 cells with almost the same efficiency ($IC_{50}$ about 1 μM). Since the Hill coefficient is about 1, the blockade appeared to occur according to a simple bimolecular reaction, i.e. one molecule of blocker interacting with one site on the $Na^+$ channel. Therefore, the $IC_{50}$ value measured the dissociation constant $K_D$ of the blockers. No effect could be demonstrated on $Ca^{2+}$ currents measured in GH3 cells and DRG neurons when using these compounds. The slight depressing effect found for trimebutine on currents is in agreement with results reported in ileal smooth muscle cells (Nagasaki et al., 1993b). In this work, it is shown that trimebutine inhibited an outward current consisting of a $Ca^{2+}$-dependent $K^+$ current (IKCa) and a $Ca^{2+}$-independent $K^+$ current (Ikv). Taken together, the most potent effects of trimebutine are found on $Na^+$ channels in neuronal or GH3 cells with $IC_{50}$ lower than 1 μM, the effects on $Ca^{++}$ or $K^+$ currents being observed at 10- to 100-fold higher concentrations. Hence, the effects of trimebutine and related compounds on $Na^+$ currents, which appears responsible for the inhibitory effect on glutamate release, indicates a potential therapeutic effect of these compounds in pain.

Sodium channel blockers like local anesthetics are known to block the generation and conduction of nerve impulses by inhibiting the current through voltage-gated $Na^+$ channels in the nerve cell-membrane (Strichartz and Ritchie, 1987). The effect of TMB and related compounds on $Na^+$ currents, which is responsible for the inhibitory effect on glutamate release, indicates a potential therapeutic effect of these compounds in pain.

Example 4

Formalin-induced Pain in Rat

The aim of this study is to evaluate the analgesic activity of TMB and its metabolites in formalin-induced pain.
4.1 Materials and Methods
a) Animals
Swiss male mice (23+/–3 grams) on test day are used; animals are acclimatised to the laboratory environment ($24°5$ C.$<t°<24°$ 8 C.) for at least one hour before testing.
b) Test
A solution of 5% formalin is prepared in sterile saline (v/v) and 20 μl is injected under the plantar surface of the left paw. Following intraplantar injection of formalin (t=o), the animals are placed in a glass cylinder and the time spent licking the injected paw is determined from t=20 to t=25 minutes after formalin injection. Drugs are given by subcutaneous route 10 minutes before the injection of formalin (30 minutes before testing); control animals received the appropriate vehicle in the same experimental conditions.
c) Data Analysis
Data are Presented as the mean+/–SEM. The statistical significance of differences between groups are obtained by means of one-way analysis of variance followed by Dunnett's comparison test with a level of significance $p<0.05$. A percentage of activity is calculated as follows:

$$\frac{\text{control mean} - \text{treated mean}}{\text{control mean}} \times 100$$

Figure 6:
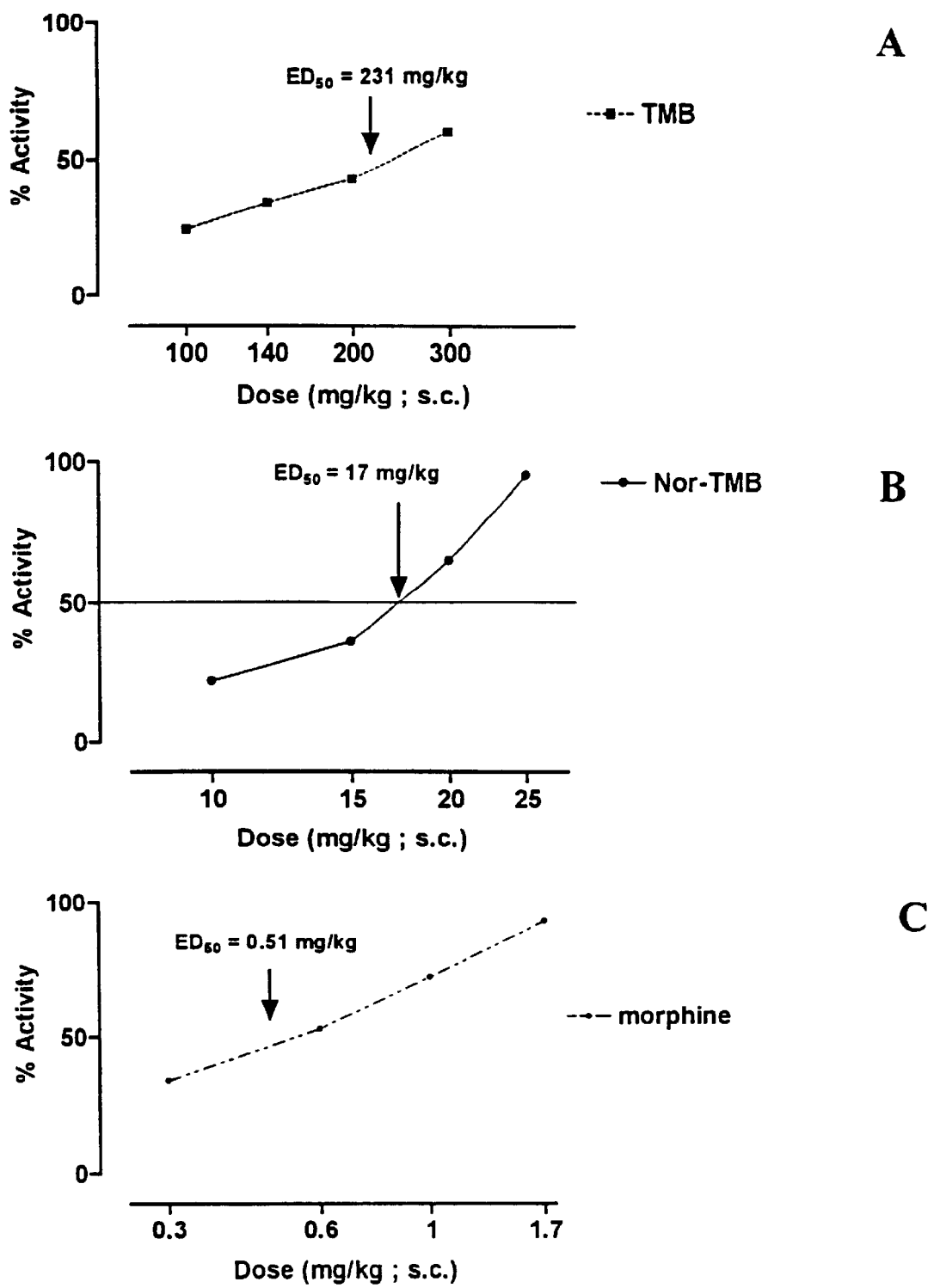
FIGS. 6(A, B, and C): Effect of TMB (A) and (S)-Nor-TMB (B) on formalin induced pain in the rat. The effect is compared to that of morphine (C). Compounds are injected s.c. at 100 mg/kg 30 min before formalin injection.

$ID_{50}$ (dose of drugs necessary to reduce the licking time by 50% relative to the control value) is calculated by the graded dose response
4.2 Results
Rats are injected s.c. with the test compounds 30 min before formalin injection in the paw TMB displayed an $ED_{50}$ of 231 mg/kg (FIG. 6A) whereas Nor-TMB (FIG. 6B) displayed an activity of 17 mg/kg. In the same experimental conditions, morphine (FIG. 6C) displayed an $ED_{50}$ of 0.51 mg/kg.

These results show that Trimebutine and its metabolites display antinociceptive properties in formalin induced pain.

Example 5

$PGE_2$-induced Hyperagesia

The aim of this study is to evaluate the antihyperalgesic activity of TMB, its stereoisomers and its metabolites in Prostaglandin $E_2$ ($PGE_2$)-induced hyperalgesia in the rat.
5.1 Materials and Methods
a) Animals
Test is carried out with Sprague-Dawley male rats (100–120 grams) on arrival. They are housed 5 per cage and acclimated to the conditions of the animal room for 5 days under a 12/12 day/night cycle and a constant room temperature of 22° C. Food and water are provided ad libidum.

b) Test
A solution of $PGE_2$ (1 mg/ml) is prepared as a stock solution in a 10% (v/v) alcohol in apyrogen sterile saline and stored at 4° C. for 4 days. A solution of $PGE_2$ (1 μg/ml) is freshly prepared twice daily in sterile saline and 100 μl is injected subplantar into the left paw of rat, twice daily for 4 days. Using this protocol, hyperalgesia is present for at least a week following completion for 4 days of treatment. Control animals (saline group) are given sterile saline in the same experimental conditions. Hyperalgesia is measured by the Randall and Selitto's test (Randall and Setillo, 1957) using an analgesimeter (Ugo Basile). The analgesimeter is basically a device which exerts a force that increases at constant rate. The force is applied to the animal's paw which is placed on a small plinth under a cone-shaped pusher. The operator depresses a pedal-switch to start the mechanism with exerts the force. The nociceptive threshold is defined as the force at which the rat withdraws its paw. The threshold is determined before and after treatment. Drugs are given by subcutaneous route, 30 minutes before the second determination; Control animals (saline and $PGE_2$ group) received the appropriate vehicle in the same experimental conditions.
c) Data Analysis
Data are presented as the mean+/–SEM.

The level of statistical significance is determined with Student's t test (Tallarrida and Murray, 1987) for paired sample and differences with $p<0.05$ are considered statistically significant. % of antinociceptive activity is calculated as follows:

$$\frac{\text{mean } PGE_2/\text{treated group after drug treatment} - \text{mean } PGE_2/\text{vehicle group after vehicle treatment}}{\text{mean saline/vehicle group after vehicle group} - \text{mean } PGE_2/\text{vehicle group after vehicle treatment}} \times 100$$

Figure 7A:
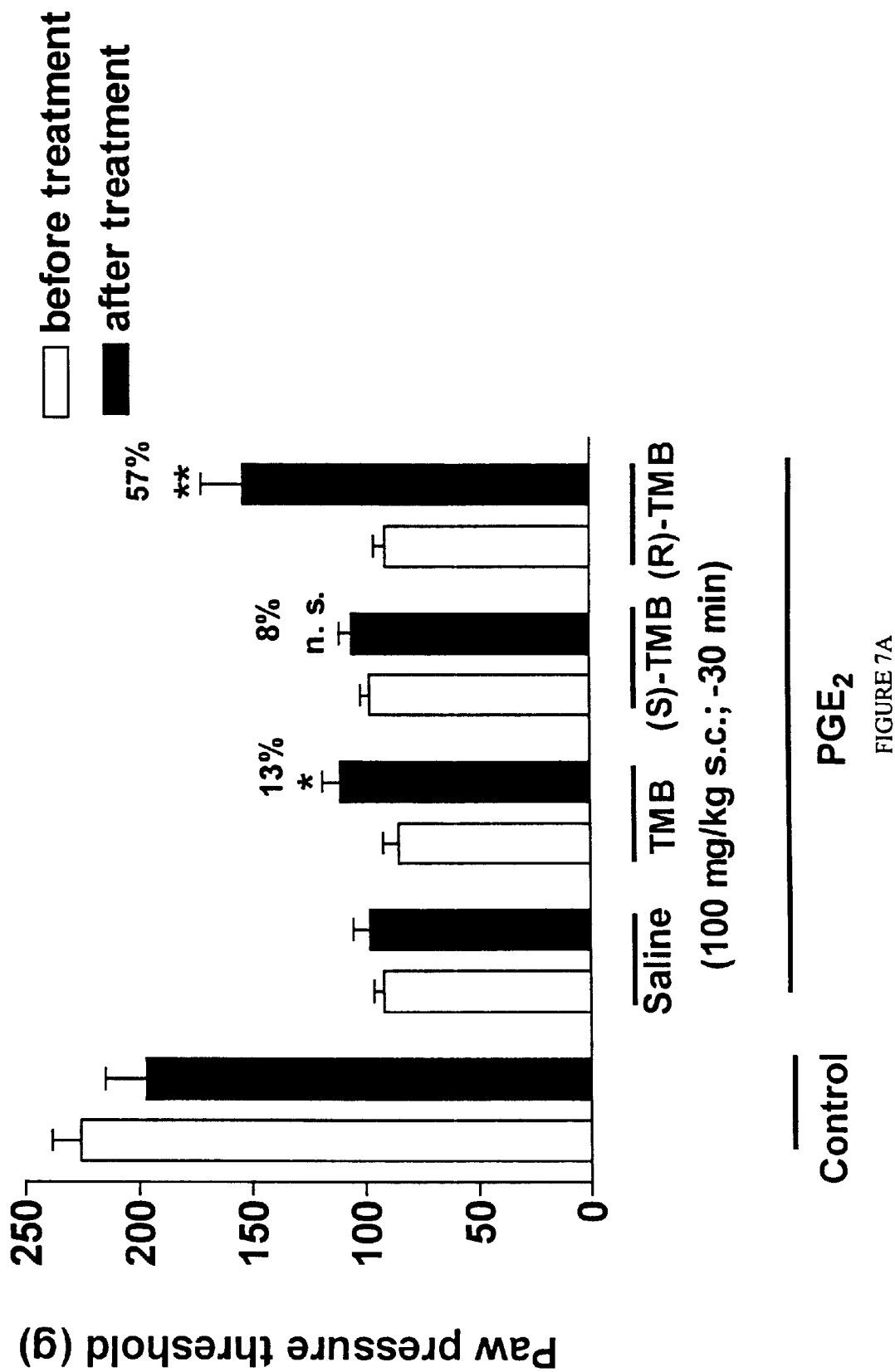
FIGS. 7A, 7B, and 7C: Effect of TMB (A), (S)-Nor-TMB (B) and morphine (C) on PGE$_2$-induced hyperalgesia. Compounds are injected s.c. at 100 mg/kg 30 min before pressure threshold evaluation.
Figure 7B:
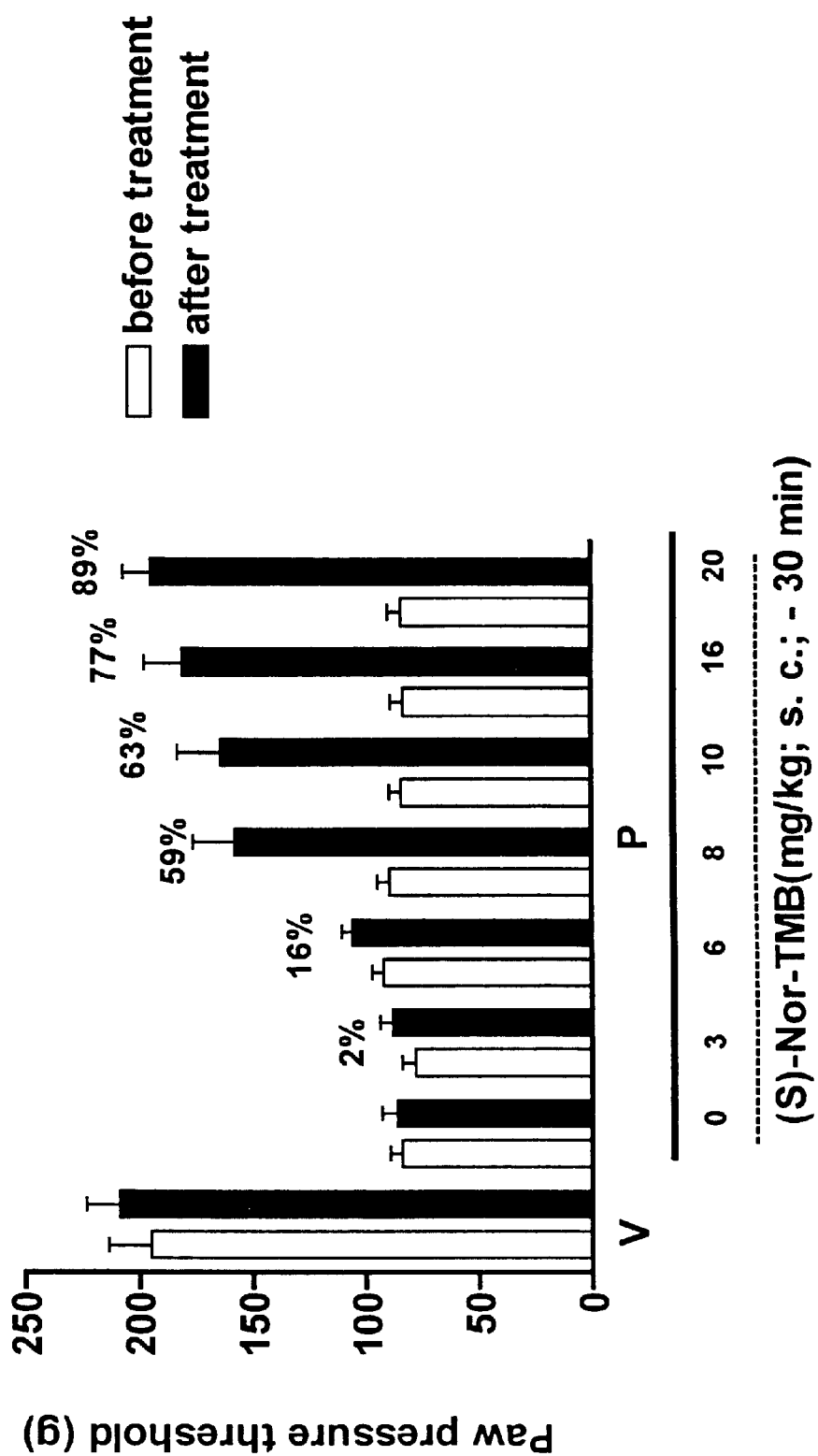
Figure 7C:
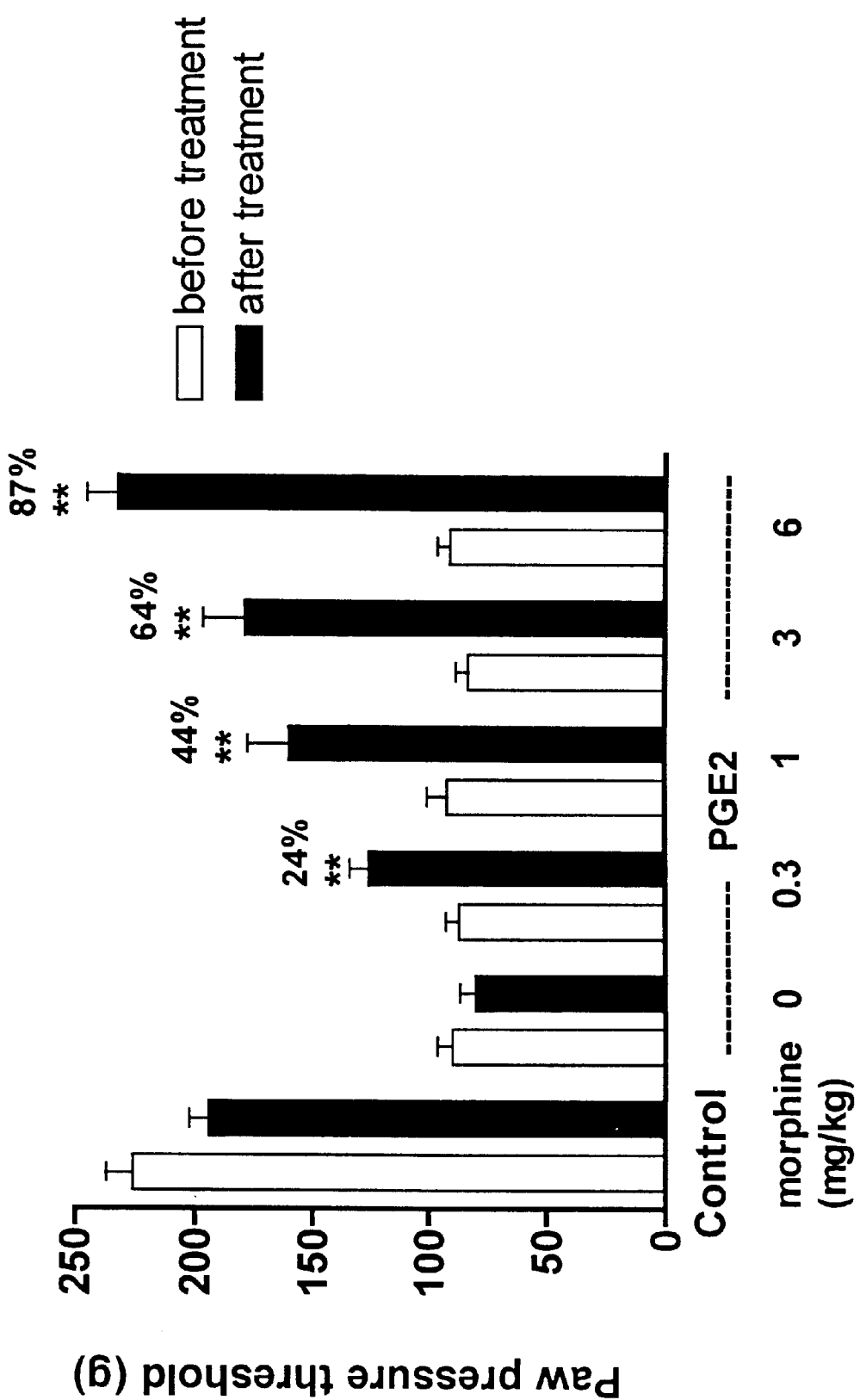

5.2 Results
According to the results shown in FIG. 7(A), (R)-TMB produced an inhibition of 57% at 100 mg/kg s.c. In the same conditions, FIG. 7(B) demonstrates that (S) Nor-TMB is able to produce an inhibition up to 89% at 20 mg/kg s.c. Accordingly, (S)-Nor-TMB displayed an $ED_{50}$ of 7 mg/kg. These results demonstrate that TMB and its metabolites are able to reverse the hyperalgesia produced by $PGE_2$.

Example 6

Rat Mononeuropathy

The aim of the study is to evaluate the metabolite of TMB in a model of rat neuropathy.
6.1 Materials and Methods
The Committee for Research and Ethical Issues of the International Association for the Study of Pain (IASP) Ethical Guidelines are adhered to in these studies. In particular, the duration of the experiments is as short as possible and the number of animals is kept to a minimum.
a) Animals
Male Sprague-Dawley rats (Charles River, France, strain designation Crl:CD(SD)BR), n=45, weighing 175–200 g on arrival are used. The rats are housed at the experimental facilities for a week prior to the experiments. They are maintained on a 12 h light/dark cycle and have free access to standard laboratory food and tap water in an ambient temperature of 20–22° C.
b) Surgery
The unilateral peripheral mononeuropathy is produced on the right hind limb according to the method described by Bennett and Xie, 1988 and Attal et al., 1990. Rats are anaesthetized with sodium pentobarbitone (Nembutal, 50 mg/kg i.p.). The common sciatic nerve is exposed by blunt dissection at the level of the mid-tigh; four ligatures (5–0 chromic catgut, about 1-mm spacing) are placed around the nerve.

c) Antinociceptive Testing

Experiments are carried out in a quiet room. Animals are not acclimatized to the test situations beforehand. The experimenter is unaware of the drug and doses used. Each animal received drugs only once and is used in only one experiment. The antinociceptive action is determined by measuring the vocalization threshold elicited by pressure on both the nerve-injured and the contralateral hindpaw, using the Ugo Basile (Comerio, Italy) analgesymeter. This instrument generates a linearly increasing mechanical force applied by a dome-shaped plastic tip (diameter=1 mm) on the dorsal surface of the paw. The tip is positioned between the third and fourth metatarsus (into the sciatic nerve territory) and force is applied until the rat squeaked. For each rat, a control threshold (mean of two consecutive stable thresholds expressed in g) is determined before injecting the drug. The vocalization thresholds are then measured every 10 min, until they returne to the level of the control values.

d) Data Analysis

Data are expressed as means±S.E.M. The areas under the curves (AUC) are calculated using the trapezoidal rule. Statistical significance of the data is analysed by one-way analysis of variance (ANOVA). The observed significances are then confirmed with Tukey's test. Simple regressions (linear model) are performed to establish dose-dependent effects. Statistical analyses are carried out using a statistical computer program (Statgraphics Plus, Manugistics, Rockville, Md.). $P<0.05$ is used as the criterion for statistical significance.

Figure 8A:
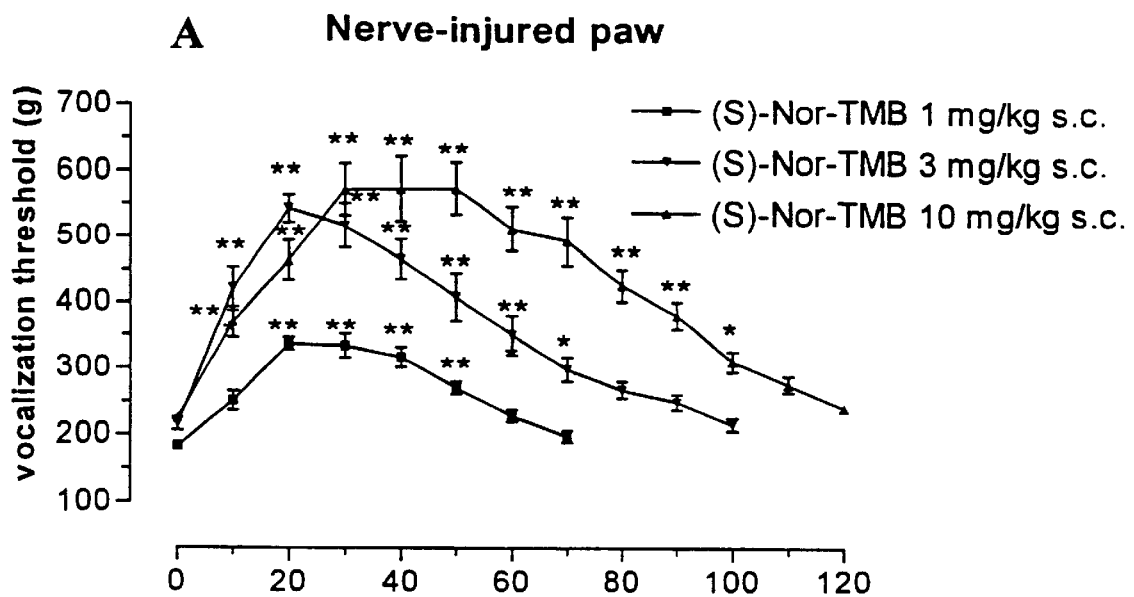
FIGS. 8A, 8B, and 8C: Effect of (S)-Nor-TMB on the vocalization threshold in the lesioned paw (A) and the contralateral paw (B) of rats with mononeuropathy. Effect of morphine in the lesioned paw (C) and in the contralateral paw (D). *P<0.05; **P<0.01
Figure 8B:
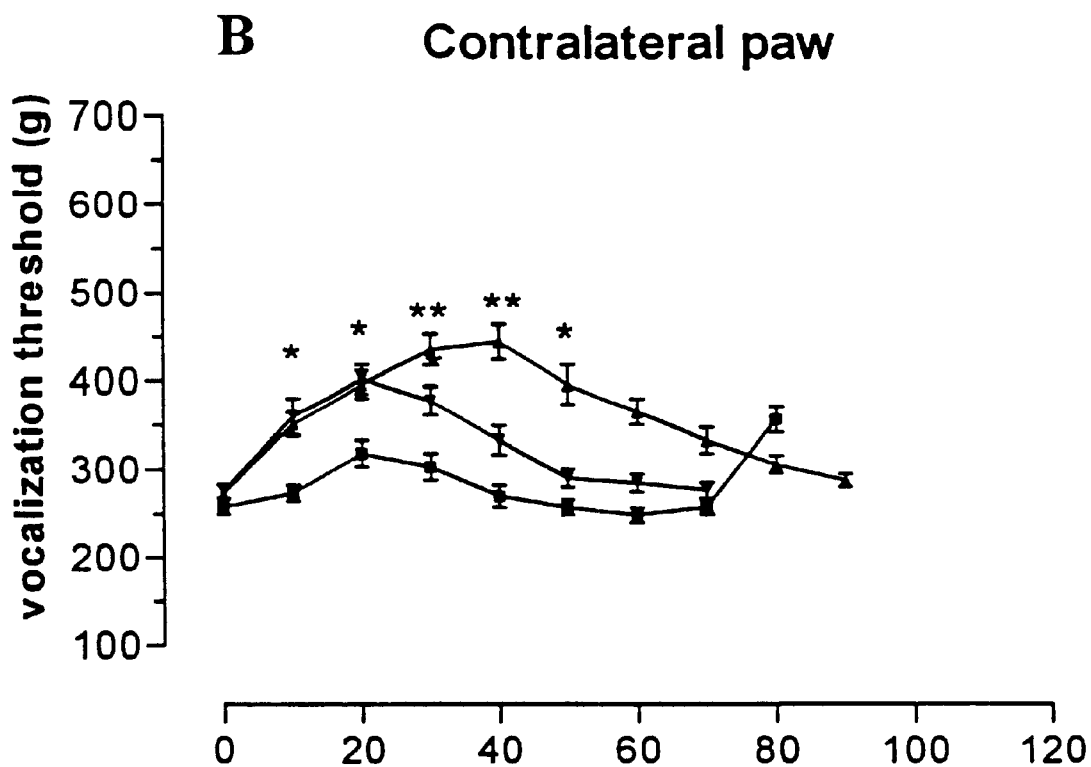
Figure 8C:
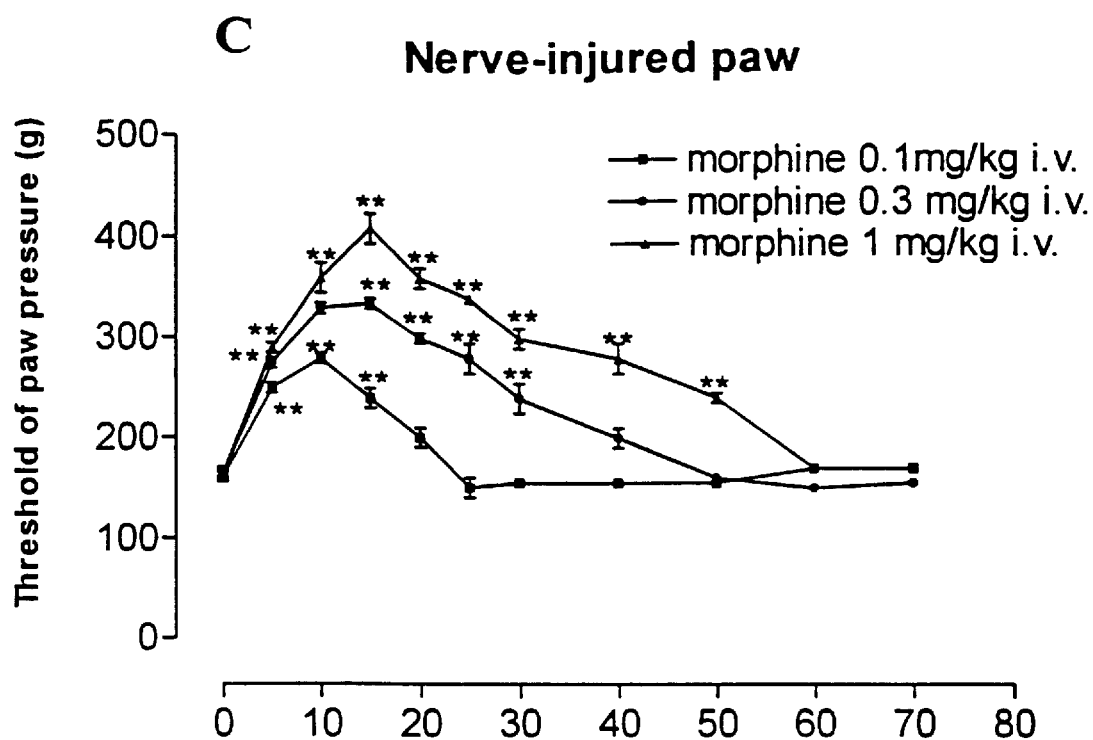
Figure 8D:
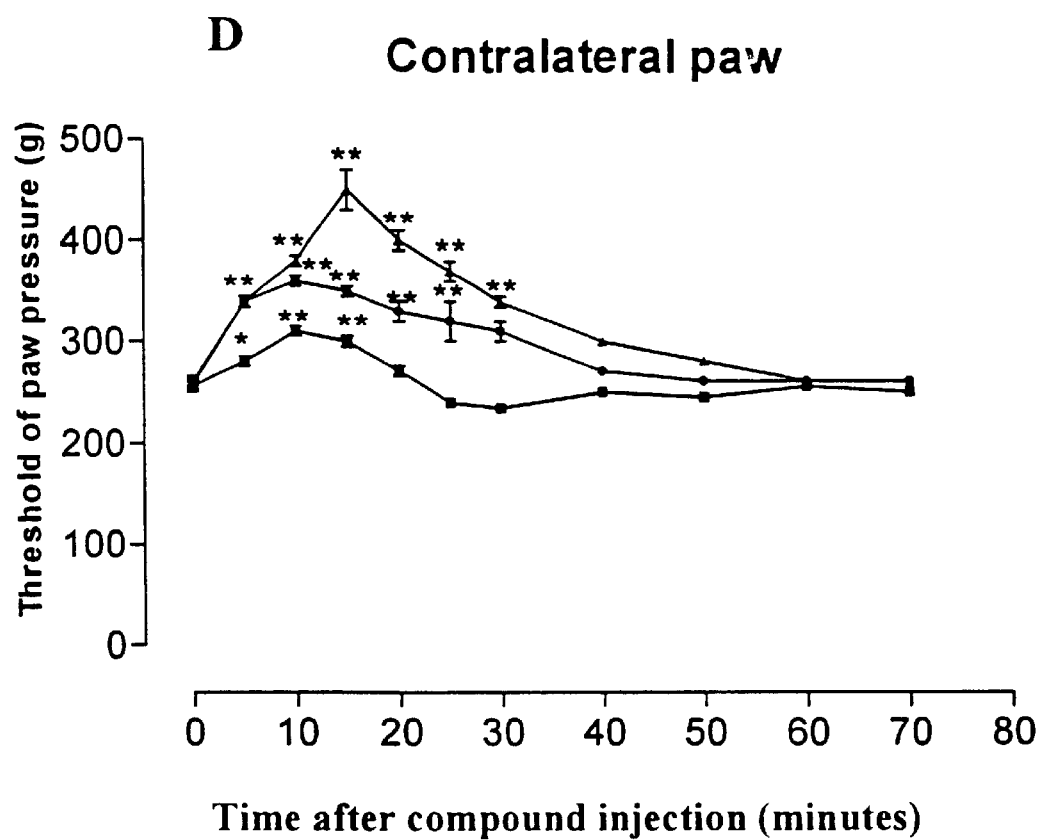

6.2 Results (S)-Nor-TMB produced an antinociceptive effect that is more pronounced in the nerve-injured paw than in the contralateral paw (FIGS. 8A and 8B). The effect is significant at all the three doses tested in the nerve-injured paw, only at the highest dose (10 mg/kg) in the contralateral paw. The antinociceptive effect lasted for more than 90 min. In the case of morphine (FIGS. 8C and D), the maximum pressure threshold obtained with the highest dose of 1 mg/kg i.v. is lower than that found with (S)-Nor-TMB 3 mg/kg s.c.; furthermore, the duration of the effect is less than 60 min with morphine and the effect in the nerve-injured paw is similar to that found in the contralateral paw. In summary, in this model of mononeuropathy, (S)-Nor-TMB at 3 and 10 mg/kg s.c. produces an antinociceptive effect that is superior to that of morphine at 1 mg/kg i.v. in terms of amplitude and of duration of action.

These results have shown that a metabolite of trimebutine, (S)-Nor-TMB is able to increase the pressure threshold necessary to produce vocalization of the rats. This effect is present from the dose of 1 mg/kg s.c. The effect obtained with (S)-Nor-TMB 3 mg/kg s.c. is more potent in terms of analgesia than that obtained with morphine 1 mg/kg i.v.

Example 7

Streptozocin-induced Diabetic Rats

The purpose of this example is to demonstrate the nociceptive effect of one metabolite of trimebutine in the model of rats Streptozocin-induced diabetes.

7.1 Material and Methods

Streptozocin is a selective pancreatic β-cell toxin, which has been used to induce experimental diabetes in laboratory animals (Tomlinson K. C. et al., 1992,). The resultant loss of endogenous insulin induced by streptozocin mimics the characteristics of type I, or insulin-dependent, diabetes. Streptozocin-induced diabetes has recently been described as a model of chronic pain in rats. It has been reported that streptozocin administration leads to mechanical, thermal, and chemical hyperalgesia as well as mechanical hypersensitivity (Courteix C. et al., 1993; Calcutt N. A. et al., 1996). The most common symptoms of diabetic neuropathy appear to be spontaneous burning pain and mechanical hypersensitivity in the feet or lower limbs.

a) Animals

Test is carried out with male Sprague Dawley rats (Iffa-Credo) weighing 160–180 grams on arrival. They are housed 5 per cage and acclimated to the conditions of the animal room for five days under a 12/12 day/night cycle and a constant room temperature of 22° C. Food and water are provided ad libidum.

b) Induction of Diabetes

Animals are intraperitoneally injected with streptozocin 75 mg/kg. Control animals are given vehicle in the same conditions. Diabetes are confirmed once a week after injection by measurement of tail vein blood glucose levels with Boehriger glycemnia test. Only animals with a final glucose level $\leq 14$ nM are included in the study.

c) Test of Tail Immersion in Water

The tail of the rat is immersed in a water bath at 44° C. Nociceptive reaction is defined as the reaction time (seconds) before the tail withdrawal. Results are expressed as the mean+/–SEM and analysed by a Student's t test after an analysis of variance (Anova one way)

7.2 Results

Figure 9:
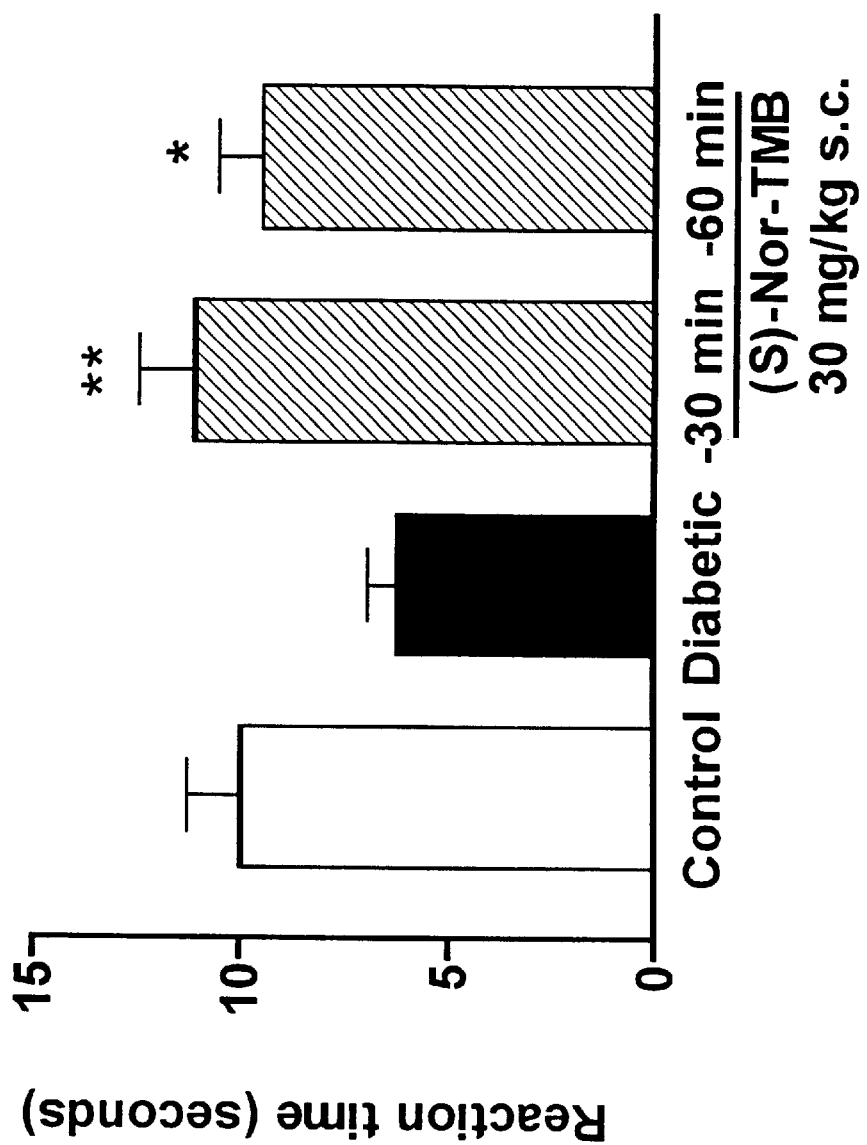
FIG. 9: Effect of TMB in diabetic rats.

Streptozocin treatment produced an hyperalgesia measured in rats as the reaction time of tail withdrawal from hot water (FIG. 9). The results show that after a single dose treatment with (S)-Nor-TMB 30 mg/kg s.c. 30 min or 60 min before tail immersion test, the reaction time is the same as in control (non diabetic) rats. These results demonstrate thus the antinociceptive effect of a metabolite of trimebutine in this model.

REFERENCES

Allescher H D, Ahmad S, Classen M and Daniel E E (1991) Interaction of trimebutine and JO-1196 (fedotozine) with opioid receptors in the canine ileum. *J Pharmacol Exp Ther* 257: 836–842.

Attal, N., Jazat, F., Kayser, V. and Guilbaud, G., Further evidence for 'pain-related' behaviours in a model of unilateral peripheral mononeuropathy, *Pain,* 41 (1990) 235–251.

Battaglia G and Rustioni A (1988) Coexistence of glutamate and substance P in dorsal root ganglion cells of the rat and monkey. *J Comp Neurol* 27: 302–312.

Bean B P, Cohen C J and Tsien R W (1983) Lidocaine block of cardiac sodium channels. *J Gen Physiol* 81: 613–642.

Bennett, G. J. and Xie, Y. K., A peripheral mononeuropathy in rat that produces disorders of pain sensation like those seen in man [see comments], *Pain,* 33 (1988) 87–107.

Bourget P and Delouis J M (1993) Review of a technic for the estimation of area under the concentration curve in pharmacokinetic analysis. *Therapie* 48: 1–5.

Bradette M, Delvaux M, Staumont G, Fioramonti G, Bueno L and Frexinos J (1994) Evaluation of colonic sensory thresholds in IBS patients using a barostat: definition of optimal conditions and comparison with healthy subjects. *Dig Dis Sci* 39: 449–57.

Bueno L, Honde C, Pascaud X and Junien J L (1987) Effects of orally versus parenterally administered trimebutine on gastrointestinal and colonic motility in dogs. *Gastroenterol Clin Biol* 11: 90B–93B.

Calcutt, N. A., Jorge, M. C., Yaksh, T. L. and Chaplan, S. R., Tactile allodynia and formalin hyperalgesia in streptozotocin-diabetic rats: effects of insulin, aldose reductase inhibition and lidocaine, *Pain,* 68 (1996) 293–299.

Cheng Y C and Prusoff W H (1973) Relationship between the inhibition constant (Ki) and the concentration of inhibitor which causes 50 percent inhibition ($IC_{50}$) of an enzymatic reaction. *Biochem Pharmacol* 22: 3099–4002.

Coderre T J and Melzack R (1992) The contribution of excitatory amino acids to central sensitization and persistent nociception after formalin-induced tissue injury. *J Neurosci* 12: 3665–3670.

Courteix, C., Eschalier, A. and Lavarenne, J., Streptozocin-induced diabetic rats: behavioural evidence for a model of chronic pain, *Pain,* 53 (1993) 81–88.

Delis C, Walker E A, Castillo F D, Evans D F, Wingate D L, Allouche S and Van Egroo L D (1994) The effect of stress and opioid agonist on postprandial motor activity in the human small bowel Digestive disease week (a) Abstract AGA, New Orleans, USA (b) *Gastroenterology* 106: A 485.

Dickenson A H (1995) Spinal cord pharmacology of pain. *British Journal of Anesthesia.* 75: 193–200.

Dray A, Urban L and Dickenson A (1994) Pharmacology of chronic pain. *Trends in Pharmacological Sciences* 15: 190–197.

Frexinos J, Fioramonti J and Bueno L (1985) Effect of trimebutine on colonic myoelectrical activity in IBS patients. *Eur J Clin Pharmacol* 28: 181–185.

Ghidini O, Saponati G and Intrieri L (1986) Single drug treatment for irritable colon: rociverine versus trimebutine maleate. *Curr Ther Res* 39: 541–548.

Grandjouan S, Chaussade S, Couturier D, Thierman-Duffaud D and Henry J F (1989) A comparison of metoclopramide and trimebutine on small bowel motility in humans. *Aliment Pharmacol Ther* 3: 387–393.

Julia V, Coelho A M, Rouzade M I, Allouche S and Bueno L (1996) Influence de la trimébutine (Débridat) sur l'hypomotricité colique et les crampes abdominales liées à la distension rectale chez le rat. *Med Chir Dig* 25: 239–242.

Lees G and Leach M J (1993) Studies on the mechanism of action of the novel anticonvulsant lamotrigine (lamictal) using primary neuroglial cultures from rat cortex. *Brain Res.* 612: 190–199.

Lüttecke K (1980) A three part controlled study of trimebutine in the treatment of irritable colon syndrome. *Cur Med Res Op* 6: 437–443.

Mao J, Price D D, Hayes R L, Lu J, Mayer D J and Frenk H (1993) Intrathecal treatment with dextrorphan or ketamine potently reduces pain-related behaviors in a rat model of peripheral mononeuropathy. Brain Research 605: 164–168.

Mc Pherson G A (1985) Analysis of radioligand binding experiments: a collection of computer programs for the IBM PC. *J Pharmacol Methods* 14: 213–228.

Meert T F and Melis W (1992) Interactions between epidurally and intrathecally administered sufentanil and bupivacaine in hydroxypropyl-β-cyclodextrin in the rat. *Acta Anesthesiol Belg* 43: 79–89.

Meunier P (1980) Effet de la trimébutine sur la motricité colique dans les colopathies. Abstract, *Gastroenterol Clin Biol* 4: 26 1A.

Moshal M G and Herron M (1979) A clinical trial of trimebutine in spastic colon. *J Int Med Res* 7: 231–234.

Nagasaki M, Komori S and Ohashi H (1993) Effect of trimebutine on voltage-activated calcium current in rabbit ileal smooth muscle cells. *Br J Pharmacol* 110: 399–403.

Nagasaki M, Komori S, Tamaki H and Ohashi H (1993) Effect of trimebutine on $K^+$ current in rabbit ileal smooth muscle cells. *Eur J Pharmacol* 235: 197–203.

Pascaud X, Roman F, Petoux F, Vauche D and Junien J L (1987) Action de la trimebutine sur la motricité gastro-intestinale. *Gastroenterol Clin Biol* 11: 77B–81 B.

Randall, L. and Selitto, J. L. (1957) Arch. Int. Pharmacodyn., 4, 409–419

Rawal N (1990) Indications for the use of intraspinal opioids, in *Spinal Narcotics* (Rawal N and Coombs D W eds) pp 43–61, Kluwer Academic Publishers, Dordrecht.

Reboa G, Bertoglio C, Terrizzi A and Parodi E (1976) L'azione della trimebutina sull'attivita elettrica e manometrica del colon normale e patologico. *Riv Gastroenterol* 28: 1–16.

Roman F, Pascaud X, Taylor J E and Junien J L (1987) Interactions of trimebutine with guinea pig opioid receptors. *J Pharm Pharmacol* 39: 404–407.

Sanguinetti M C and Kass R S (1984) Voltage-dependent block of calcium channel current in the calf cardiac purkinje fiber by dihydropyridine calcium channel antagonists. *Circ Res* 55(3): 336–348.

Schang J C, Devroede G and Pilote M (1993) Effect of trimebutine on colonic function in patients with chronic idiopathic constipation: evidence for the need of a physiologic rather than clinical selection. *Dis Colon Rectum* 36: 330–336.

Strichartz G and Ritchie J (1987) The action of local anesthesics on ion channels of excitable tissues in *Local Anesthesics Handbook of Experimental Pharmacology* (Strichartz G ed) pp 21–52, Springer-Verlag, Heidelberg.

Tallarida R. J and Murray R. B. (1987) Manual of Pharmacological Calculations with Computer programs Taniyama K, Sano I, Nakayama S, Matsuyama S, Takeda K, Yoshihara C and Tanaka (1991) Dual effect of trimebutine on contractility of the guinea pig ileum via the opioid receptors. *Gastroenterology* 101: 1579–1587.

Tomlinson, K. C., Gardiner, S. M., Hebden, R. A. and Bennett, T., Functional consequences of streptozotocin-induced diabetes mellitus, with particular reference to the cardiovascular system, *Pharmacol Rev,* 44 (1992) 103–150.

Toussaint J, Cremer M and Pintens H (1981) Etude en simple aveugle de trimébutine et de la mébévérine dans le cólon irritable et la dyspepsie *Acta Ther* 7: 261–268.

Triggle D J (1997) Stereoselectivity of drug action [review]. *Drug Discovery Today* 2: 138–147.

Turner T J and Dunlap K (1995) Prolonged time course of glutamate release from nerve terminals: relationship between stimulus duration and the secretory event. *J Neurochem* 64: 2022–2033.

Urban L, Thompson S W N and Dray A (1994) Modulation of spinal excitability: co-operation between neurokinin and excitatory amino acid neurotransmitters. *Trends Neurosci* 17(10): 432–438.

Valmier J, Simmoneau M and Boisseau S (1989) Expression of voltage-dependent sodium and transient potassium currents in an identified subpopulation of dorsal root ganglion cells acutely isolated from 12-day-old mouse embryos. *Pflügers Arch* 414: 360–368.

Wang H, Kunkel D D, Schwartzkroin P A and Tempel B L (1994) Localization of Kv1.1 and Kv1.2, two K channel proteins, to synaptic terminals, somata, and dendrites in the mouse brain. *J Neurosc* 14; 4588–4599.

Wermelskirchen D, Wilffert B and Peters T J (1992) Veratridine-induced intoxication: an in vitro model for the characterization of anti-ischemic compounds. *Basic Clin Physiol Pharmacol* 3: 293–321.

What is claimed is:

1. A method for preventing or treating arthritis, comprising administering to a patient in need thereof a pharmaceutical composition containing trimebutine, or a corresponding stereoisomer thereof, and a pharmaceutically acceptable carrier or excipient.

2. A method for preventing or treating osteo-traumatic pain, comprising administering to a patient in need thereof a pharmaceutical composition containing trimebutine, or a corresponding stereoisomer thereof, and a pharmaceutically acceptable carrier or excipient.

3. A method for preventing or treating neuralgias, comprising administering to a patient in need thereof a pharmaceutical composition containing trimebutine, or a corresponding stereoisomer thereof, and a pharmaceutically acceptable carrier or excipient.

4. A method for preventing or treating post-herpetic neuralgia, comprising administering to a patient in need thereof a pharmaceutical composition containing trimebutine, or a corresponding stereoisomer thereof, and a pharmaceutically acceptable carrier or excipient.

* * * * *